(12) United States Patent
Shapiro et al.

(10) Patent No.: US 10,466,227 B2
(45) Date of Patent: Nov. 5, 2019

(54) SENSING AND ACTUATION OF BIOLOGICAL FUNCTION USING ADDRESSABLE TRANSMITTERS OPERATED AS MAGNETIC SPINS

(71) Applicant: CALIFORNIA INSTITUTE OF TECHNOLOGY, Pasadena, CA (US)

(72) Inventors: Mikhail Shapiro, Los Angeles, CA (US); Azita Emami, Pasadena, CA (US); Manuel Alejandro Monge Osorio, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 15/882,281

(22) Filed: Jan. 29, 2018

(65) Prior Publication Data

US 2018/0164276 A1 Jun. 14, 2018

Related U.S. Application Data

(62) Division of application No. 14/561,114, filed on Dec. 4, 2014, now Pat. No. 9,915,641.

(60) Provisional application No. 61/911,856, filed on Dec. 4, 2013.

(51) Int. Cl.
*G01N 33/46* (2006.01)
*G01R 17/00* (2006.01)
*G01R 33/07* (2006.01)
*A61B 5/00* (2006.01)
*A61B 5/04* (2006.01)
*A61B 5/07* (2006.01)
*A61B 5/1459* (2006.01)
*G01N 33/483* (2006.01)
*H04B 1/40* (2015.01)
*G01R 33/12* (2006.01)
*A61B 5/05* (2006.01)

(52) U.S. Cl.
CPC ......... *G01N 33/483* (2013.01); *A61B 5/0522* (2013.01); *G01R 33/077* (2013.01); *G01R 33/1284* (2013.01); *H04B 1/40* (2013.01); *A61B 5/073* (2013.01); *G01R 33/1269* (2013.01)

(58) Field of Classification Search
CPC ...... G01N 33/46; G01N 33/483; G01R 17/00; G01R 33/077; A61B 5/00; A61B 5/04; A61B 5/073; A61B 5/05; A61B 5/07; A61B 5/1459
See application file for complete search history.

(56) References Cited

U.S. PATENT DOCUMENTS

| 9,915,641 | B2 | 3/2018 | Shapiro et al. | |
| 2009/0318761 | A1* | 12/2009 | Rabinovitz | A61B 1/00158 600/118 |
| 2010/0321163 | A1* | 12/2010 | Stevenson | A61N 1/056 340/10.1 |
| 2012/0238810 | A1* | 9/2012 | Kobayashi | A61B 1/0005 600/109 |

(Continued)

*Primary Examiner* — Neel D Shah
(74) *Attorney, Agent, or Firm* — Steinfl + Bruno LLP

(57) ABSTRACT

Methods and apparatuses for sensing biological functions are disclosed. Sensors can be implanted in an organ, such as the brain, and a magnetic field gradient applied to the biological tissue. The field causes the sensors to have different resonant frequencies allowing their spatial localization. The sensors can harvest power from the external coils to be able to retransmit data.

4 Claims, 43 Drawing Sheets

(56) References Cited

U.S. PATENT DOCUMENTS

| | | | |
|---|---|---|---|
| 2013/0166002 A1* | 6/2013 | Jung | A61N 5/00 |
| | | | 607/100 |
| 2014/0296666 A1* | 10/2014 | Rabinovitz | A61B 5/1459 |
| | | | 600/310 |
| 2015/0153319 A1 | 6/2015 | Shapiro et al. | |
| 2015/0170504 A1* | 6/2015 | Jooste | A61B 5/6898 |
| | | | 340/539.12 |
| 2017/0202479 A1* | 7/2017 | Khait | A61B 5/062 |

\* cited by examiner

SENSING AND ACTUATION OF BIOLOGICAL FUNCTION USING ADDRESSABLE TRANSMITTERS OPERATED AS MAGNETIC SPINS

CROSS REFERENCE TO RELATED APPLICATIONS

The present application is a divisional of U.S. application Ser. No. 14/561,114 filed on Dec. 4, 2014 which claims priority to U.S. Provisional Patent Application No. 61/911,856 filed on Dec. 4, 2013, the disclosures of both of which are incorporated herein by reference in their entirety.

TECHNICAL FIELD

The present disclosure relates to biological sensors. More particularly, it relates to sensing and actuation of biological function using addressable transmitters operated as magnetic spins.

BRIEF DESCRIPTION OF DRAWINGS

The accompanying drawings, which are incorporated into, and constitute a part of, this specification, illustrate one or more embodiments of the present disclosure and, together with the description of example embodiments, serve to explain the principles and implementations of the disclosure.

SUMMARY

Figure 1:
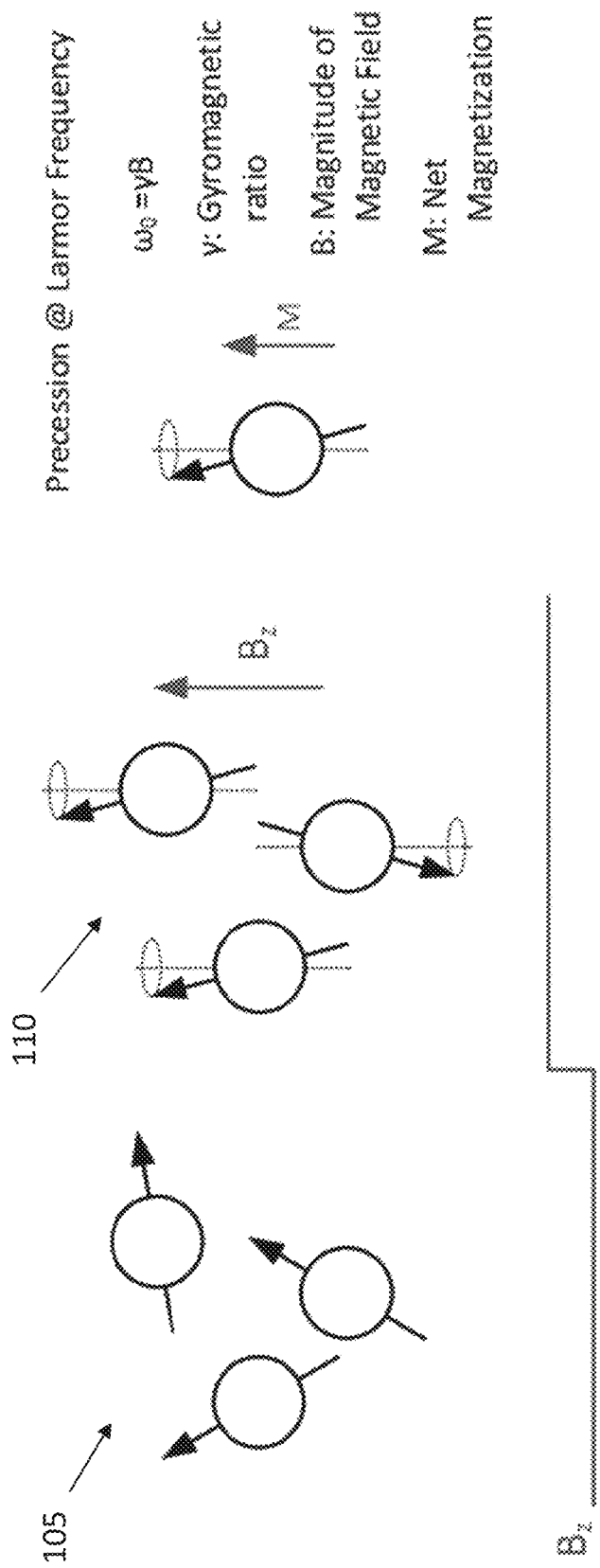
FIG. 1 illustrates the concept of precession of magnetic spins.

In a first aspect of the disclosure, a communication device is described that includes a substrate, an antenna, a transmitter and receiver, a control logic circuit, and at least one sensor, which may be a magnetic sensor. The antenna may be configured to transmit and receive electromagnetic waves at a first frequency and a first phase between the device and a communication device. The transmitter and receiver circuit may be configured to operate the antenna. At least one sensor may be configured to sense an applied magnetic field and to shift a transmitting or receiving frequency from the first frequency to a second frequency, or a transmitting or receiving phase from the first phase to a second phase. The shift may be based on the applied magnetic field. The dimensions of the antenna and the oscillator circuit may be configured to allow spatial localization of the device when the device is within a magnetic field gradient.

In a second aspect of the disclosure, a system is described that includes a communication device as heretofore described and at least one magnetic field generator, configured to generate a linear or a nonlinear magnetic field gradient, and at least one radio frequency coil for transmitting and receiving electromagnetic waves.

In a third aspect of the disclosure, a method to sense a biological function is described. The method includes providing a device to be implanted in a biological tissue, wherein the device includes a biological function sensor, an oscillator circuit configured to change its resonance frequency upon application of a magnetic field, and providing a communication device external to the biological tissue and configured to communicate through electromagnetic waves with the device implanted in the biological tissue. The disclosed method further includes inserting the device into a biological tissue, applying a magnetic field gradient to the device, and spatially locating the device by its resonance frequency.

In a fourth aspect of the disclosure, a second method to sense a biological function is described. This second method includes providing a system having a plurality of devices to be implanted in a biological tissue, wherein each device includes a biological function sensor, an oscillator circuit configured to change its resonance frequency upon application of a magnetic field, a communication device external to the biological tissue and configured to communicate through electromagnetic waves with the plurality of devices implanted in the biological tissue. This second method further includes inserting the plurality of devices into biological tissue, applying a magnetic field gradient to the plurality of devices, and spatially locating each device by its resonance frequency.

DETAILED DESCRIPTION

An important line of research in contemporary science envisions introducing miniature devices into the human body to diagnose and treat localized disease. Major advances have been made towards this vision, but the practical implementation of microscale biological sensors and actuators is still largely missing from in vivo biology and medicine. Meanwhile, the need for such devices is increasing due to a greater appreciation that many prevalent diseases involve local pathology (for example, neurodegeneration, cancer, psychiatric disease, and atherosclerosis) requiring local diagnosis and treatment. Notably, the recently launched national BRAIN initiative to map the function of the mammalian brain has created demand for distributed microscale sensors enabling large-scale recording of neural activity.

Microscale sensors may require the means to (a) convert local (in the body) physiological information into electrical signals, (b) transmit these signals to external receivers (outside the body), and (c) be localized to specific parts of the body and distinguished from each other. Substantial progress has been made on the first two requirements. For example, miniaturized devices have been developed to measure action potentials and neurotransmitters, the release of tumor antigens, and the presence of viral pathogens. In addition, advances in integrated circuits and antennae have led to the development of devices that are smaller, more energy-efficient and capable of high-bandwidth data transfer. The requirement that transmitters be effectively localized and distinguished from each other, however, is currently poorly addressed because existing localization schemes based on receiver proximity have limited precision and poor scaling. This is a significant limitation for scenarios ranging from individual localization of implantable biosensors and intravascular guidewire to distributed implantable sensors of neural activity and immune cell-internalized reporters homing to diseased tissues. In fact, in these and other applications, it may be necessary to distinguish between different sensors, for example to determine what region of the organ within the body their reading values are coming from.

In particular, there are currently no effective means to precisely determine the location of microscale devices deep inside the body and communicate with them in a location-specific manner. Existing methods based on near-field radio-frequency (RF) electromagnetic interactions have only a limited ability to localize and communicate with individual implants because the strong dependence of RF signals on tissue properties (specifically, body composition) drastically reduces their spatial resolution, and makes it difficult to interface with multiple devices at once. Meanwhile, localization using imaging procedures, such as x-ray computed tomography, exposes patients to ionizing radiation and can only visualize and not transmit information to and from devices at specific locations in the body.

To address the problem of microscale device localization, inspiration can be taken from one of the most successful technologies in biomedicine: magnetic resonance imaging (MRI). MRI measures signals from nuclear spins (typically aqueous hydrogen atoms), each of which can be thought of as an atomic-scale transmitter resonating at a frequency dependent on the magnetic field. The ability of MRI to distinguish the locations of more than $10^{26}$ such transmitters in the body with about 100 μm precision is based on the Nobel prize-winning insight of Paul Lauterbur. Lauterbur found that magnetic field gradients can "encode" the location of nuclei via the frequency of their signals. If a spatial magnetic field gradient is applied such that nuclei in one location resonate at a predictably different frequency from nuclei at another location, these frequency differences can be used to map the observed signals in space. Conversely, it is possible to excite nuclei selectively by applying field gradients during frequency-specific transmission.

FIG. 1 illustrates the concept of precession of magnetic spins. A set of randomly oriented nuclei spins (105) aligns and precesses (110) when an external magnetic field is applied. The spins align in the same direction as the applied magnetic field, and they precess with a known frequency, producing a net magnetization. This frequency is called Larmor frequency and is defined by the gyromagnetic ratio of the nuclei and the magnitude of the applied magnetic field.

Figure 2:
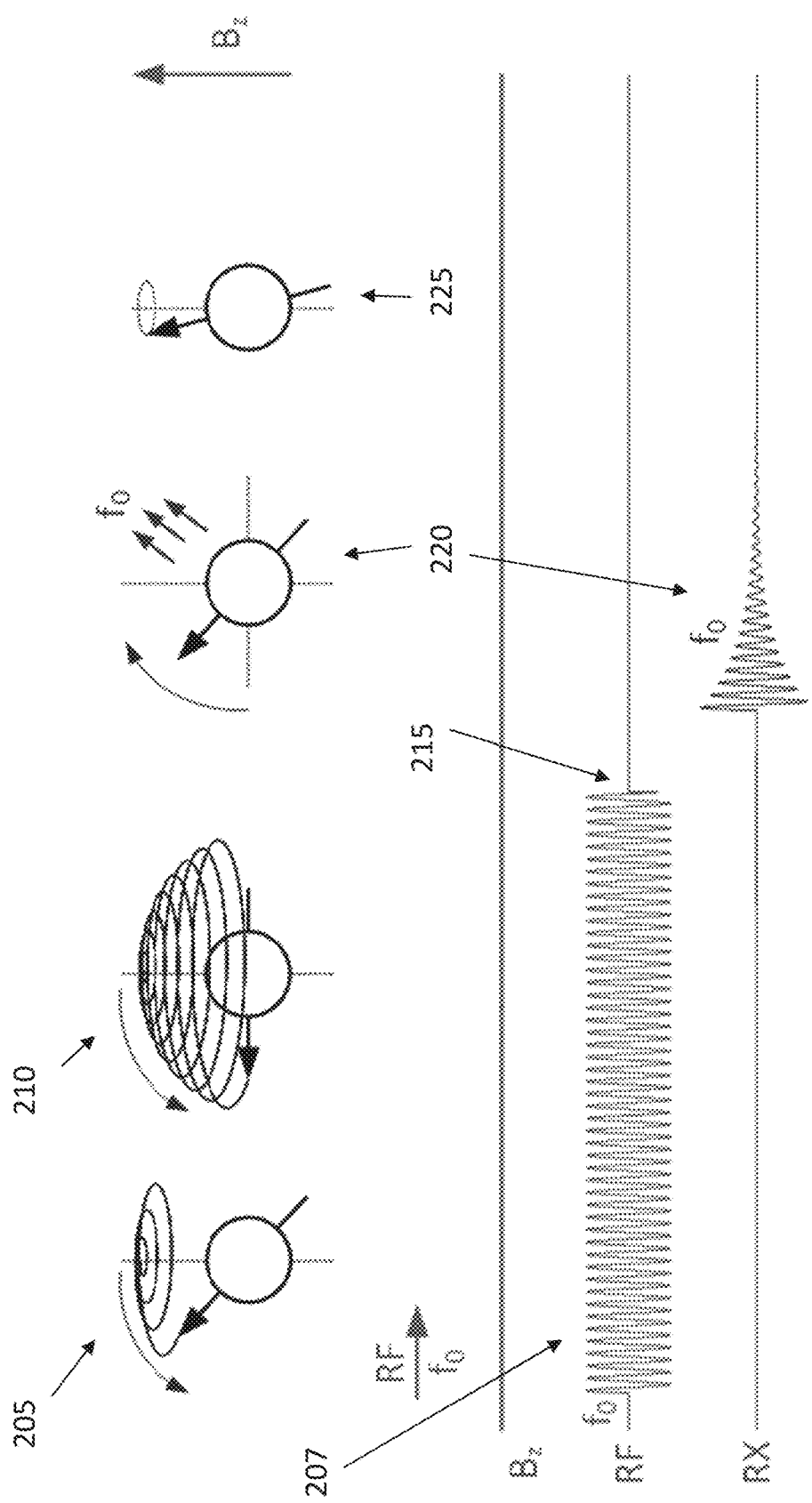
FIG. 2 illustrates the concept of magnetic resonance.

FIG. 2 illustrates the concept of magnetic resonance. When a spin precessing (205) at the Larmor frequency ($f_0$) receives a radio frequency (RF) magnetic field (207) at the same frequency $f_0$, the spin absorbs this energy and starts rotating (210). This rotation (210) depends on the duration of the RF field (207). After the excitation signal (207) is removed (215), the spin relaxes to return to the resting state (225) and radiates energy (220) at the $f_0$. This signal is then received by the magnetic resonance imaging (MRI) receiver to detect the presence of the nuclei.

Figure 3:
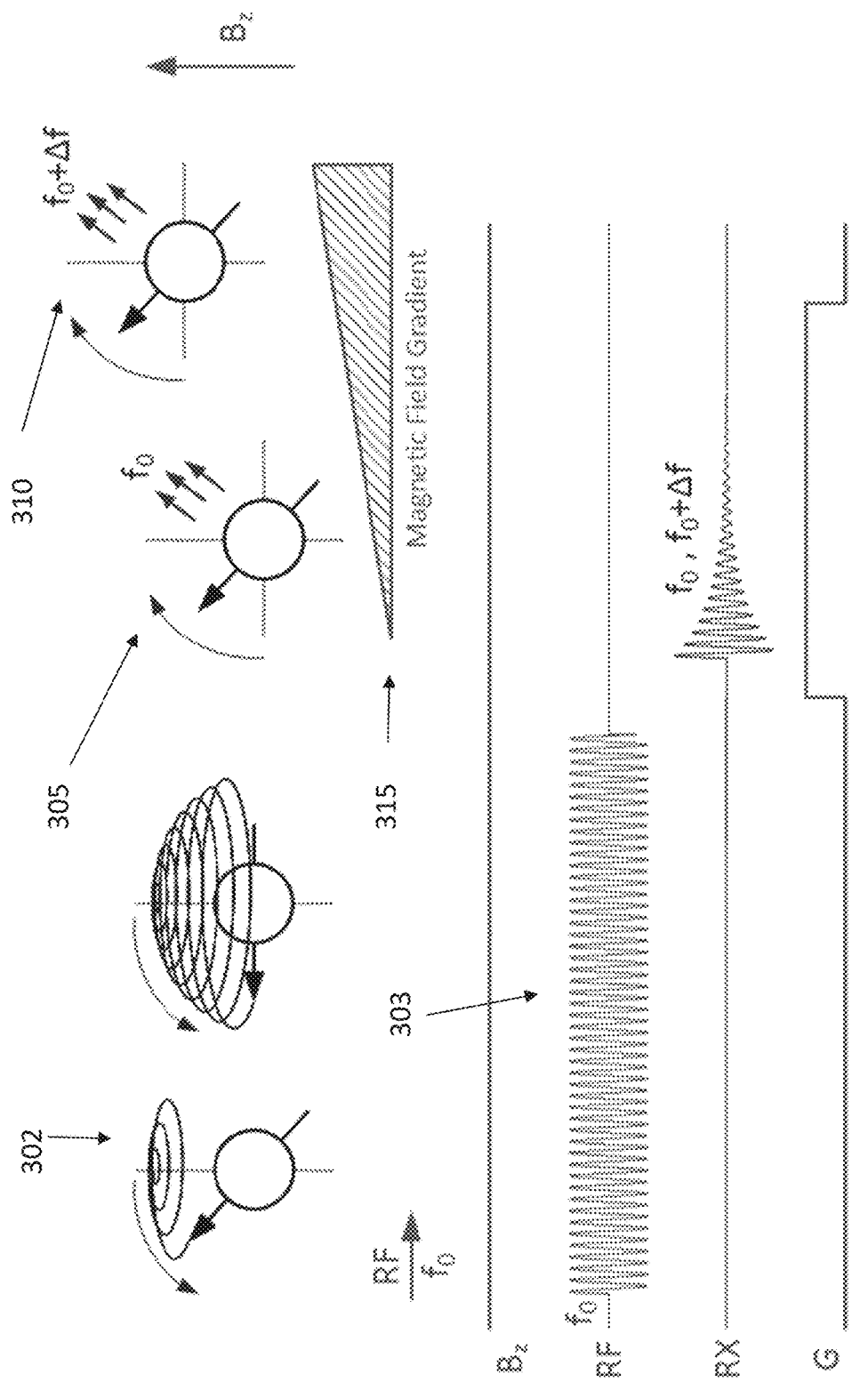
FIG. 3 illustrates the concept of spatial encoding.

FIG. 3 illustrates the concept of spatial encoding. Similarly to the concept described above, each spin precesses at the Larmor frequency (302) and receives an RF magnetic field (303). In spatial encoding, two nuclei at different locations resonate at different frequencies, $f_0$ (305) and $f_0+\Delta f$, (310), when a gradient magnetic field (315) is applied along the spatial location where the spins are located. The magnitude of the frequency shift ($\Delta f$) depends on the strength of the applied gradient field (315) and the spatial separation between the two nuclei.

In the present disclosure, methods and systems are described to adopt Lauterbur's principle to localize individual and distributed microsensors in vivo. In particular, the present disclosure describes a class of microscale transceivers that resonate at frequencies dependent on the magnetic field.

Figure 4:
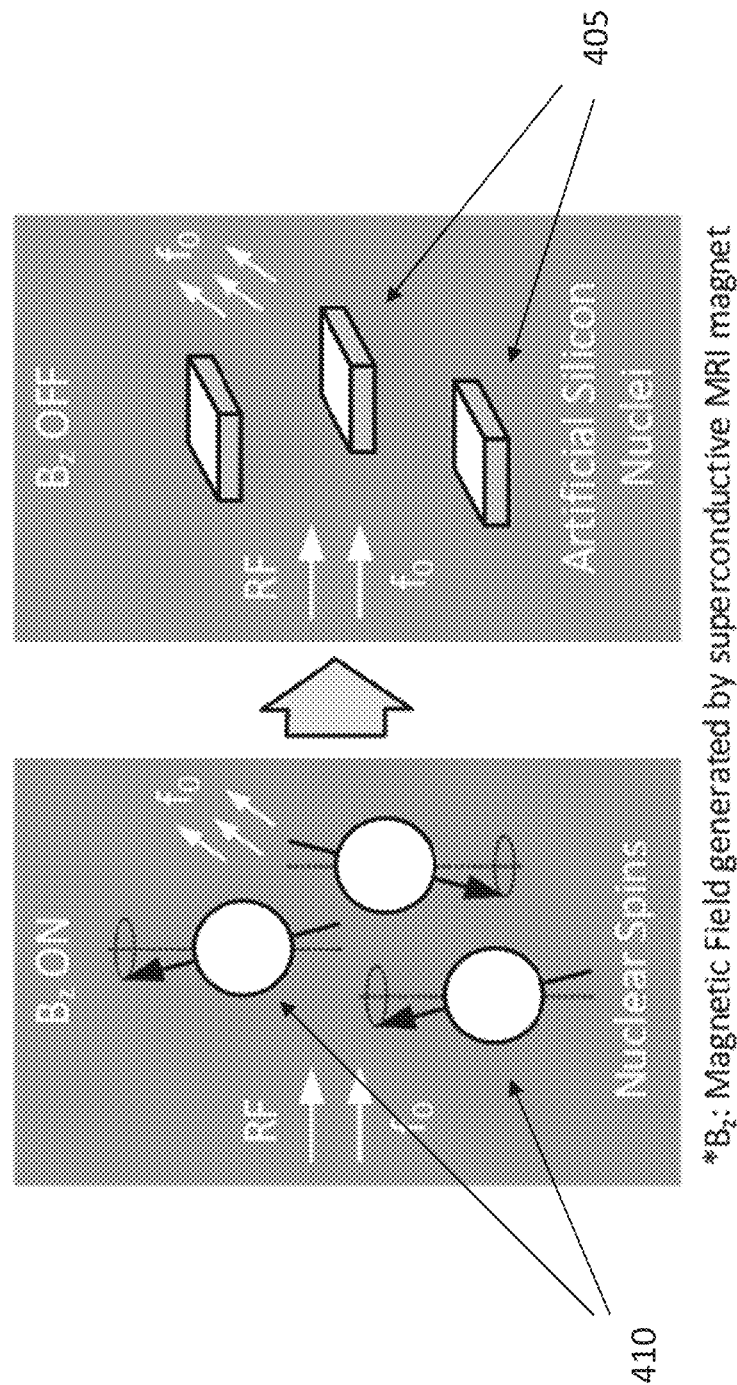
FIG. 4 illustrates the bio-inspired design of the artificial silicon "nuclei" that mimic the behavior of spins in an MRI.

FIG. 4 illustrates an exemplary bio-inspired design of the artificial silicon "nuclei" (405) that mimic the behavior of spins (410) in an Mill. Thus, the silicon devices oscillate at an RF frequency ($f_0$), with a frequency shift (Of) based on the gradient magnetic field, and radiate at the shifted frequency ($f_0+\Delta f$) after the RF magnetic field is turned off. In other words, the devices (405) of FIG. 4 behave in a manner analogous to that of the spins as illustrated in FIG. 3, enabling spatial differentiation of each device (405) because of the shifted frequency of each device (405) originating from the magnetic field gradient. These microscale integrated transducers (405) operate at magnetic field-dependent frequencies, enabling their use for localization and communication (between the implanted devices and an external device) in vivo using magnetic field gradients. Because the devices operate analogously to magnetic spins, this technology can be referred to as Addressable Transmitters Operated as Magnetic Spins (hereinafter, "ATOMS").

ATOMS can be integrated with a wide range of microscale biological sensing and actuation technologies, enabling localized recording of biochemical or bioelectrical signals, release of therapeutic agents, electrical stimulation, tissue sampling or ablation, and enabling a wide variety of biomedical applications. Thus, ATOMS has the potential to be the enabling technology for in vivo individual and distributed sensing and control of biological processes with precise localization.

Figure 5:
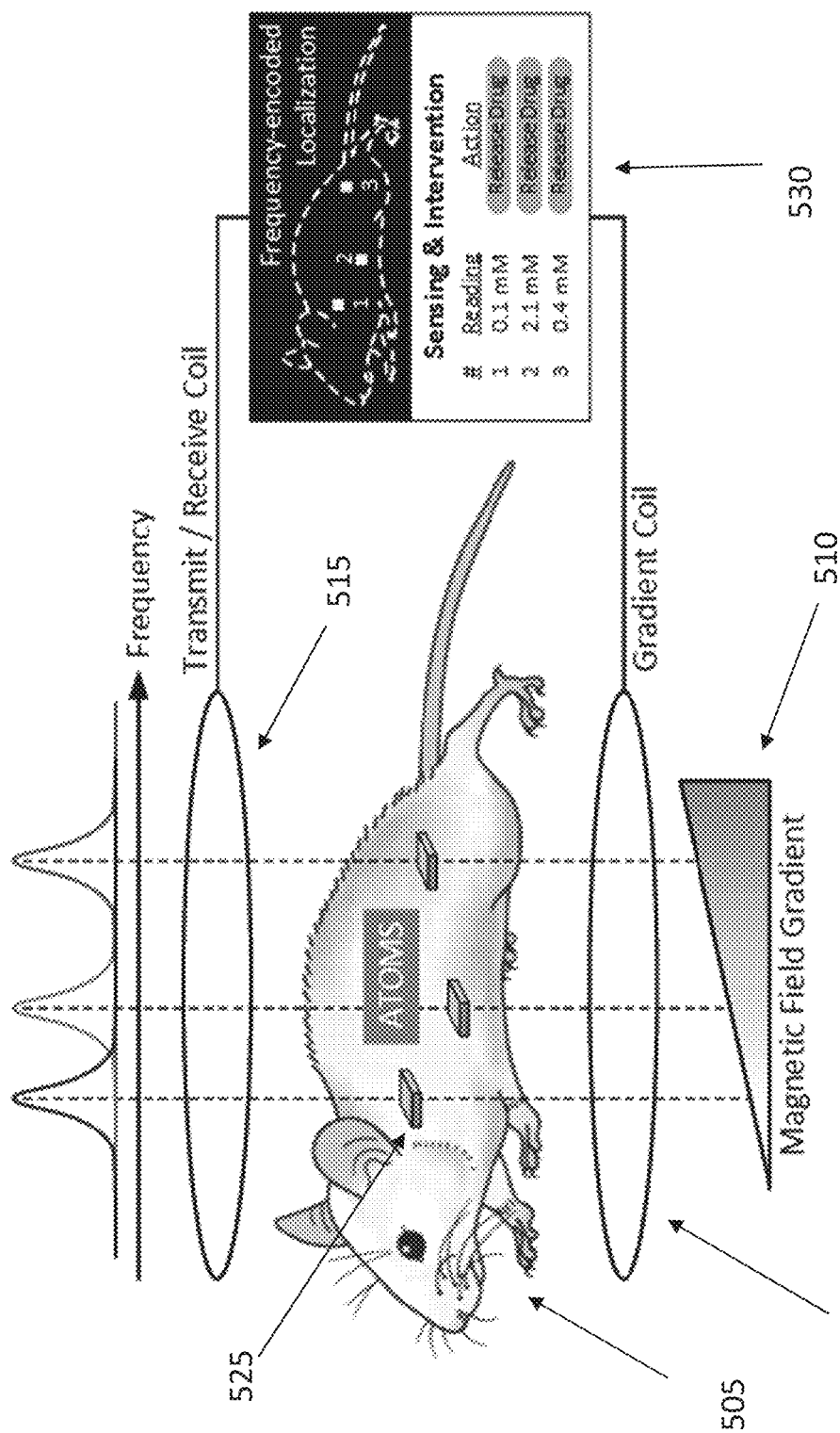
FIG. 5 illustrates an exemplary overview of the systems and methods of the present disclosure.

FIG. 5 illustrates an exemplary overview of the systems and methods of the present disclosure. ATOMS are microscale devices capable of power harvesting and communication at magnetic field-dependent frequencies. When a single or multiple ATOMS are in an animal (505) or patient, their locations can be discerned by applying a magnetic field gradient (510) and communicating (515) with them at correspondingly shifted frequencies.

For example, a coil (520) external to the animal (505) or patient could be used to generate the magnetic field gradient (510) and a second coil (515) could be used to transmit an RF magnetic field and receive the resultant signal from the ATOMS devices (525). The external coils (520, 515) generate the magnetic fields. The transmit/receive coil (515) produces the RF magnetic field and the gradient coil (520) produces the magnetic field gradient (510). In some embodiments, the magnetic field gradient (510) varies through space and is a DC field. Using the coils (520, 515), the external interface system (530) can transmit power to the implants (525) and communicate with the devices sending commands and receiving data.

Figure 6:
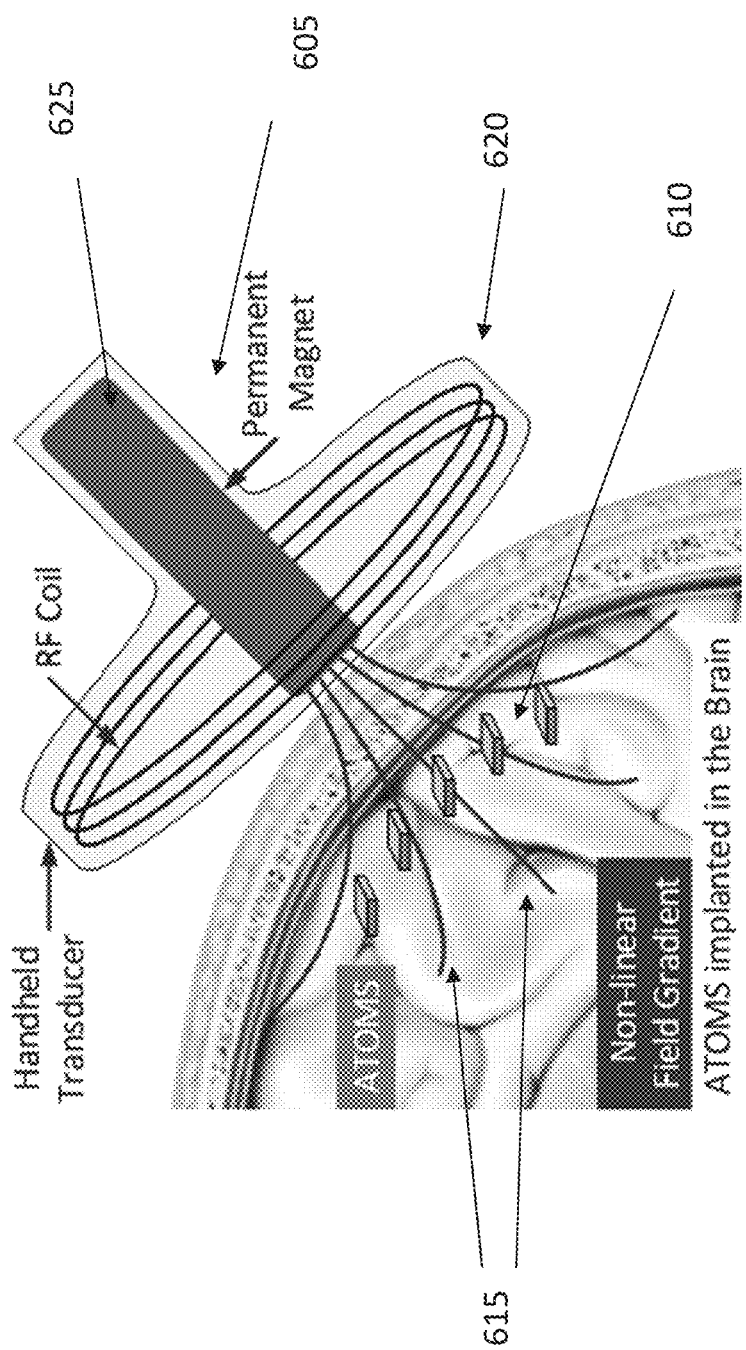
FIG. 6 illustrates a handheld transducer for localization and communication with ATOMS using a non-linear magnetic field gradient.

FIG. 6 illustrates a handheld transducer (605) for localization and communication with ATOMS implanted in a brain, using a non-linear magnetic field gradient (615). For generating non-linear gradients, a permanent magnet (625) can be used for ATOMS technology. A portable RF coil (620) can generate the RF magnetic field. Thus, a hand-held transducer (605) is envisioned which can be used, for example, for outpatient ambulatory deployment.

ATOMS can be a general-purpose platform for biological interfaces because they can provide wireless communication with precise localization, can be coupled to biological sensing and actuation circuits, can integrate electrical circuits for recording of bio-signals and for stimulation of cells, and can be coupled, for example, to micro-scale sensors (such as glucose, pressure, etc.) and actuators (such as drug release).

Therefore, ATOMS have the potential to be the enabling technology for in vivo sensing and control of biological processes with precise localization.

Figure 7:
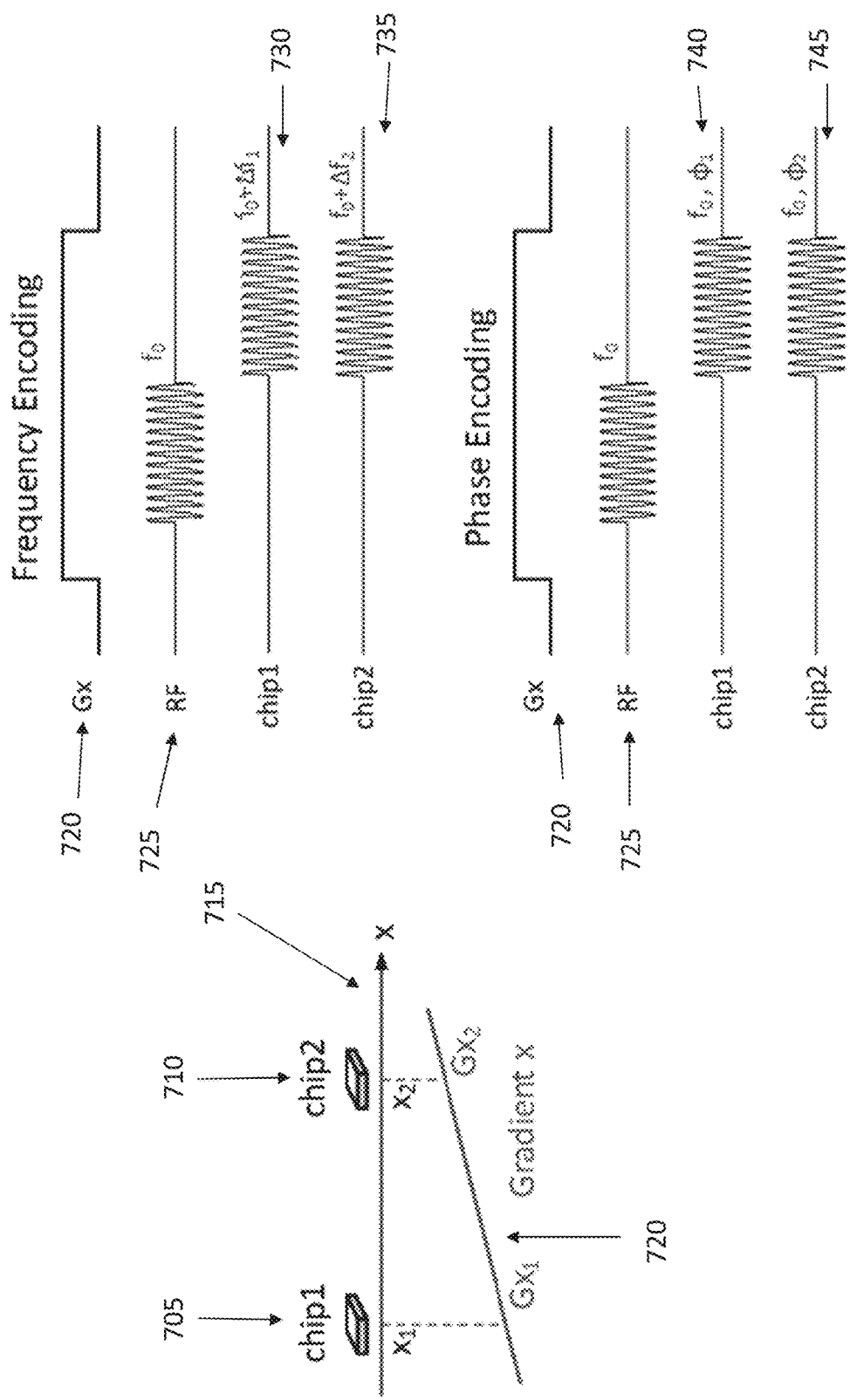
FIG. 7 illustrates a basic encoding sequence for ATOMS technology.

FIG. 7 illustrates an exemplary basic encoding sequence for ATOMS technology. This encoding sequence and the following sequences are intended as examples, and the person skilled in the art will understand that different sequences may be used. In FIG. 7, two ATOMS devices (705, 710) at different locations on the same X-axis (715) are stimulated with a magnetic field gradient Gx (720) and an RF magnetic field at frequency $f_0$ (725). Analogously to MRI, the location information can be encoded in the frequency or phase of the RF magnetic field. Subsequently, after the excitation signal (725) is removed, both devices radiate two different RF signals which can be $f_0+\Delta f_1$ (730) and $f_0+\Delta f_2$ (735), or $f_0+\phi_1$ (740) and $f_0+\phi_2$ (745), if frequency encoding or phase encoding has been used, respectively. FIG. 7 illustrates encoding on a single axis as an example. The sensing ATOMS devices, however, can be located in three dimensions, therefore encoding sequences that discern between three different axes can be used.

Figure 8:
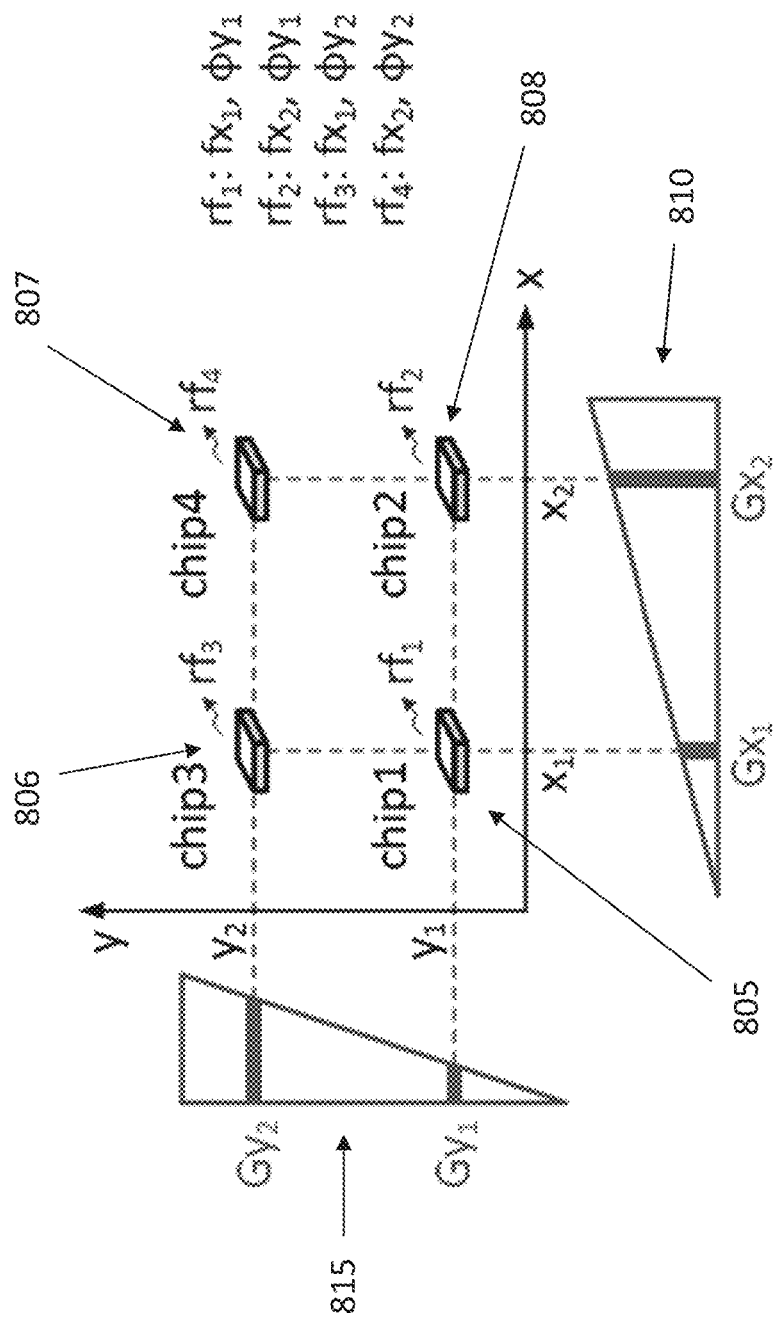
FIG. 8 illustrates the concept of 2D encoding for ATOMS technology.

FIG. 8 illustrates the concept of two-dimensional (2D) encoding for ATOMS technology. In this arrangement, four devices (805, 806, 807, 808) at different locations in the same plane XY are stimulated with magnetic field gradients Gx and Gy in both axes (810, 815) and an RF magnetic field at frequency $f_0$. Using a similar method as the one shown in FIG. 7, location information is encoded in frequency or phase, for the X-axis and Y-axis respectively. Thus, each device radiates a different signal with different frequency and different phase. For example, one device (805) might radiate at a first frequency and first phase, another device (806) might radiate at the first frequency and a second phase, another device (807) might radiate at a second frequency and the second phase, and another device (808) might radiate at the second frequency and first phase. Other combinations may be used where each device radiates at a specific frequency and phase in order to be distinguished from the remaining devices.

A similar concept for encoding as to that described above can be extended to a third dimension, allowing 3D encoding of ATOMS technology. Each device can radiate at a specific frequency and phase to be individually identified.

Because of their similarities with magnetic spins, ATOMS can be tested using standard MM instrumentation. In particular, a set of gradient coils and transmit-receive coils will be operated outside the bore of the MRI magnet. This configuration approximates other possible external interfaces for ATOMS technology, in which no static magnetic field is necessary, reducing the cost by more than a factor of 10 compared to a full MRI machine. A 500 MHz small MM system located at the Beckman Institute in Caltech is used as an example in the following exemplary description. A preliminary characterization of this exemplary system indicates that a sub-millimeter size device would be able to harvest 2 mW of power from the MRI's transmit coil and would need to produce a signal of 20 nW to be detected by the receive coil. To operate within the bandwidth of the system, the exemplary device should exhibit frequency shifts of ±0.008% (±40 kHz) centered at 500 MHz over a field strength of ±0.55 mT. The person skilled in the art will understand that devices with different characteristics to the example above may be used.

The present disclosure describes methods and systems for ATOMS technology to (a) fabricate magnetic-field dependent transmitter circuits operating at frequencies of tens to hundreds of MHz, (b) apply methods for the sensitive and precise detection and localization of the transmitters using magnetic field gradients, and (c) simultaneously monitor several such sensors in organs, human or animal.

These microscale devices are built using integrated circuits (ICs) capable of wireless communication and energy harvesting at magnetic field-dependent frequencies while requiring low power to operate, and having a small size which makes the devices easier to implant. The devices can be designed and implemented in a standard complementary metal-oxide semiconductor (CMOS) process through methods known to the person skilled in the art. In some embodiments, in order to enhance the resolution and make the chips minimally invasive, the target size of the chips can be less than one square millimeter. As explained below, the small size of the chip can have an impact on design parameters.

Some of the functions that the devices are designed to carry out can comprise: 1) harvesting sufficient power from the existing RF signal to power all the IC's functions, including sensing and actuation of biological processes, 2) sense the magnitude of the magnetic field to provide localization information, 3) use this information to produce a signal with a frequency shift or phase shift from the existing RF signal, 4) transmit/radiate this signal after the excitation RF signal is removed, 5) synchronization of multiple devices to operate at the same initial frequency and phase of the existing RF signal prior to applying the frequency shift or phase shift, and 6) calibration and adaptation to the operational environment.

Different techniques for sensing the magnetic field can be used. For example, magnetic field effect transistors (MAGFET) based on the Hall-effect could be used. The MAGFET can be designed and optimized in a target CMOS process, where the differential output current of the device can be amplified and converted to a voltage signal. Similarly, a Hall-plate implemented in a target CMOS process can also be used. These devices are sensitive to the magnetic field orthogonal to the sensor's plane.

Figure 9:
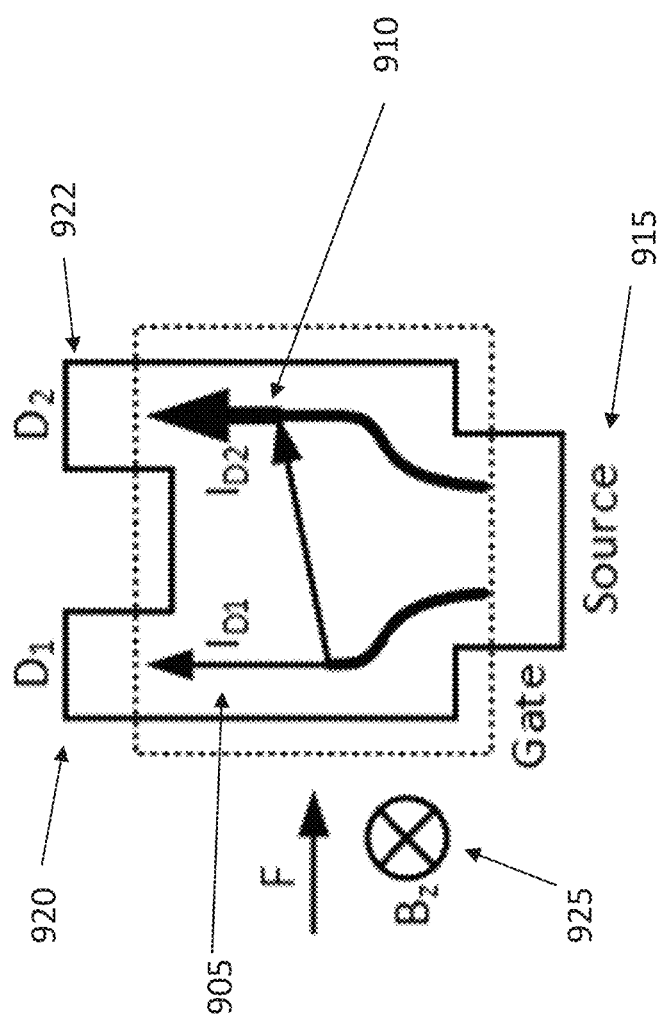
FIG. 9 illustrates the behavior of a split-drain MAGFET.

FIG. 9 illustrates the behavior of a split-drain MAGFET. In this transistor, the normally connected drain terminal is split into two drains, $D_1$ (920) and $D_2$ (922). When no magnetic field is applied, the carriers injected in the source terminal (915) travel through the device and are evenly divided between both drains (920, 922) such that $I_{D1}$ (905) is equal to $I_{D2}$ (910). When a perpendicular magnetic field (925) is applied, the carriers traveling through the devices are deflected due to the Lorentz's force. Thus, a current difference is created between $I_{D1}$ (905) and $I_{D2}$ (910) that is proportional to the applied magnetic field (925). This current difference is known as the Hall current $I_H$.

Figure 10:
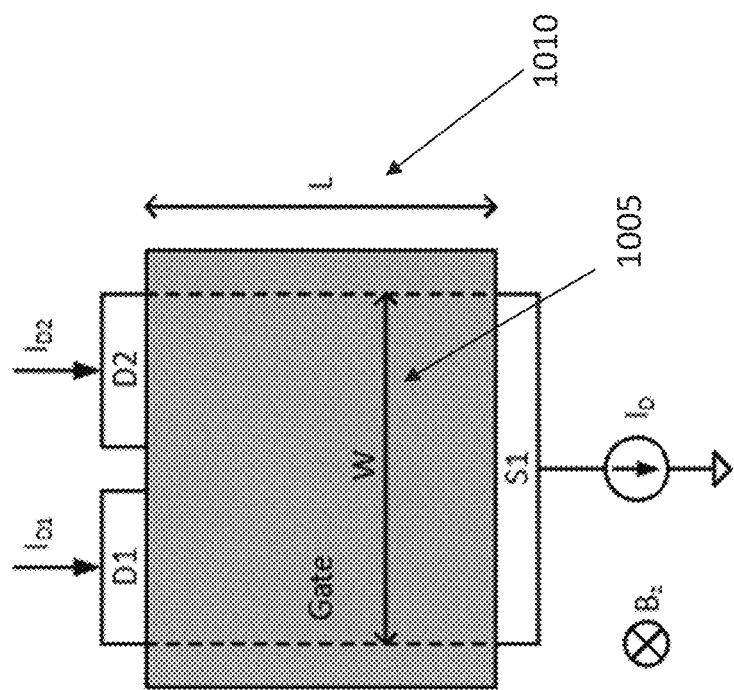
FIG. 10 illustrates a MAGFET of width (W) and length (L).

FIG. 10 illustrates a MAGFET of width (W) (1005) and length (L) (1010). The expression for the Hall current ($I_H$) and the sensitivity ($S_I$) of the sensor are known to the person skilled in the art, and are:

$$I_H = I_{D2} - I_{D1} = \mu_H B_Z \left(\frac{L}{W}\right) I_D G_H$$

-continued
$$S_I = \frac{I_H}{I_D B_Z} = \mu_H \left(\frac{L}{W}\right) G_H$$

where $\mu_H$ is the Hall mobility, $I_D$ is the drain current, $G_H$ is the geometric factor, and $B_Z$ is the applied perpendicular magnetic field.

Figure 11:
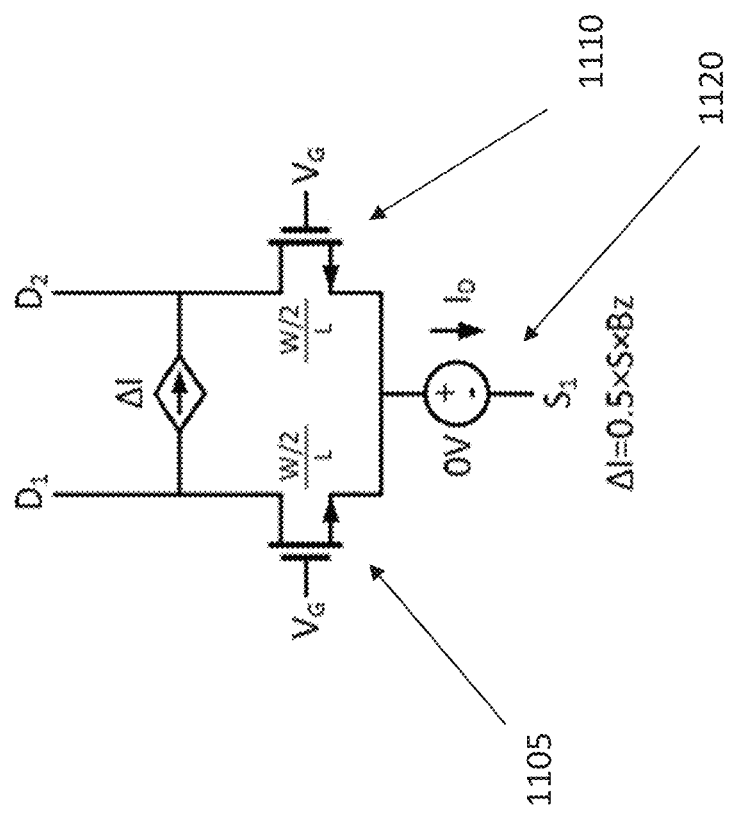
FIG. 11 illustrates the equivalent electrical model of the MAGFET of FIG. 10.

FIG. 11 illustrates the equivalent electrical model of the MAGFET of FIG. 10. The equivalent model comprises two switches (1105, 1110) and a current generator (1120).

Figure 12:
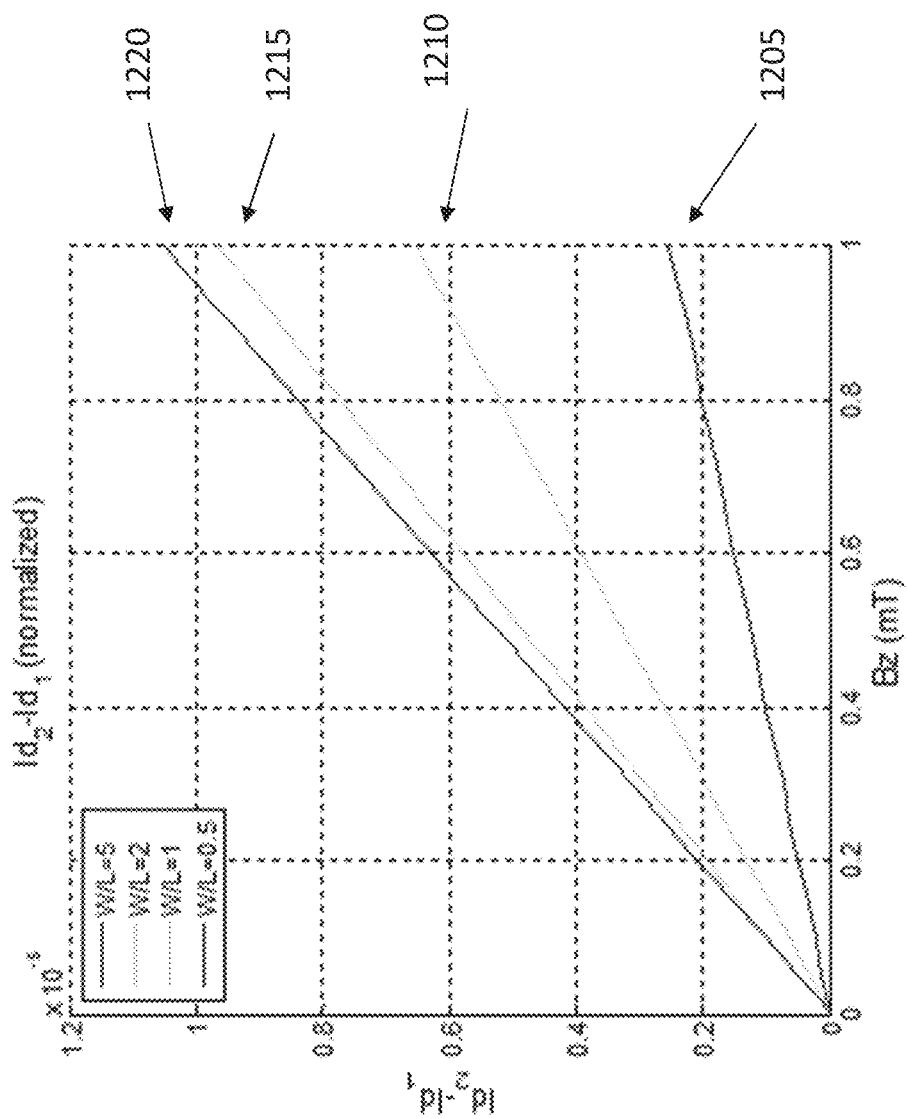
FIG. 12 illustrates simulation results of a MAGFET with different aspect ratios for a 65 nm CMOS technology using first-order approximations of the process parameters.

FIG. 12 illustrates simulation results of a MAGFET with different aspect ratios W/L for a 65 nm CMOS technology using first-order approximations of the process parameters. It can be seen that a sensitivity of about 1% per Tesla can be achieved for an aspect ratio of W/L=1. The aspect ratios of FIG. 12 are W/L=5 (1205), 2 (1210), 1 (1215) and 0.5 (1220).

Figure 13:
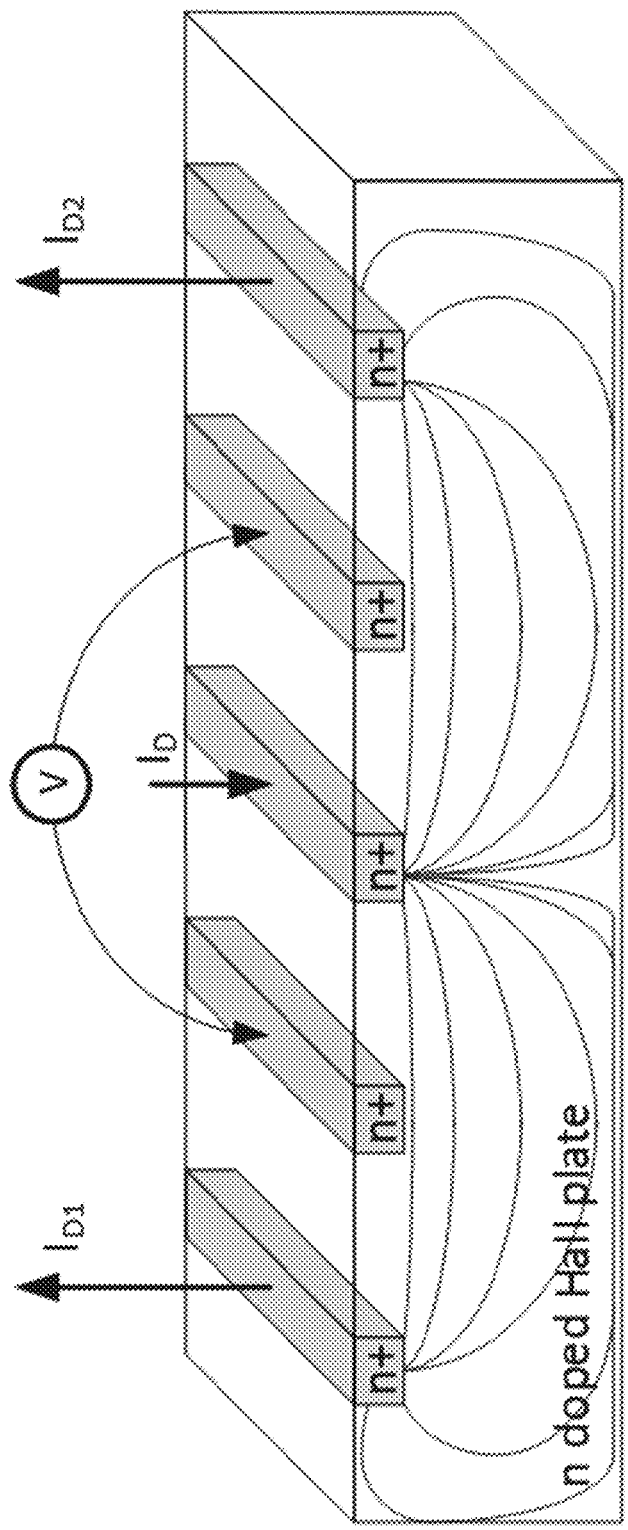
FIG. 13 illustrates the conceptual model of vertical Hall device.

FIG. 13 illustrates an exemplary conceptual model of a vertical Hall device. The behavior of this device is analogous to the behavior of the previously described MAGFET and Hall plate, known as horizontal Hall devices, but this device is instead sensitive to the in-plane magnetic field. This device can also be used to sense the magnetic field.

The output of a Hall device (magnetic sensor) can be used to change the capacitance of an inductor-capacitor (LC) oscillator using, for example, a MOS varactor. Any of the above examples for magnetic sensors can be used in the devices of the present disclosure, as well as other examples known to the person skilled in the art.

Figure 14:
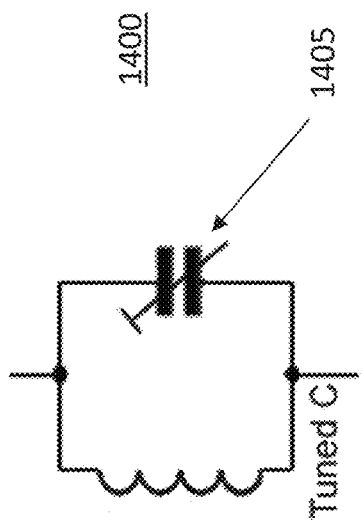
FIG. 14 illustrates an LC oscillator where a variable capacitor (varactor) is used to change the oscillation frequency.

FIG. 14 illustrates an LC oscillator (1400) where a variable capacitor (varactor, 1405) is used to change the oscillation frequency of the oscillator.

Another method for sensing the magnetic field involves the use of paramagnetic materials. For example, after removing the passivation layer over an inductor, a thin-film paramagnetic material or paramagnetic beads can be deposited over the inductor. Thus, under the presence of a magnetic field, the effective inductance of the inductor varies with the applied magnetic field. Therefore, by using this inductor in an LC oscillator, the oscillation frequency of the resonator can be changed by applying a magnetic field.

Figure 15:
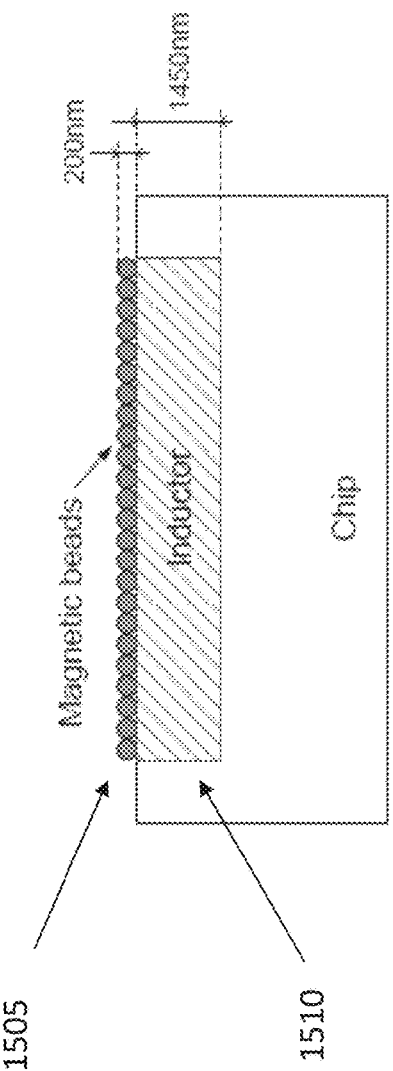
FIG. 15 illustrates an exemplary embodiment with magnetic beads deposited on an inductor.

FIG. 15 illustrates an exemplary embodiment of an oscillator with magnetic beads (1505) deposited on an inductor (1510). Magnetic beads (1505) such as those used for this example are described in P. C. Fannin et al., "Investigation of the complex susceptibility of magnetic beads containing maghemite nanoparticles", J. Mag. and Mag. Mat. vol. 303, pp. 147-152 2005, the disclosure of which is incorporated herein by reference in its entirety.

In some embodiments, the magnetic beads may have a diameter of 200 nm. In some embodiments, the beads may have an active magnetic core of about 10 nm radius on average. In some embodiments, the thickness of the inductor may be 1450 nm. Other dimensional values may be used. In this embodiment, the inductance varies as a function of the magnetic field.

Figure 16:
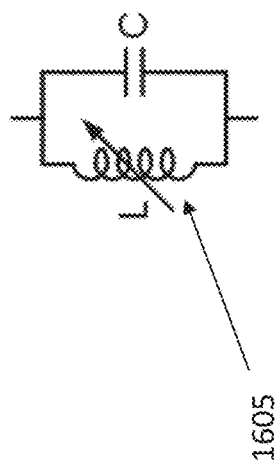
FIG. 16 illustrates an exemplary equivalent electrical circuit of the embodiment of FIG. 15.

FIG. 16 illustrates an exemplary equivalent electrical circuit of the embodiment of FIG. 15, where the inductor (1605) has a varying inductance. As understood by the person skilled in the art, with either a capacitance or inductance change, depending on the circuit used, the shift in the resonance frequency of an oscillating circuit, as explained above, can be used to detect a magnetic field.

Figure 17:
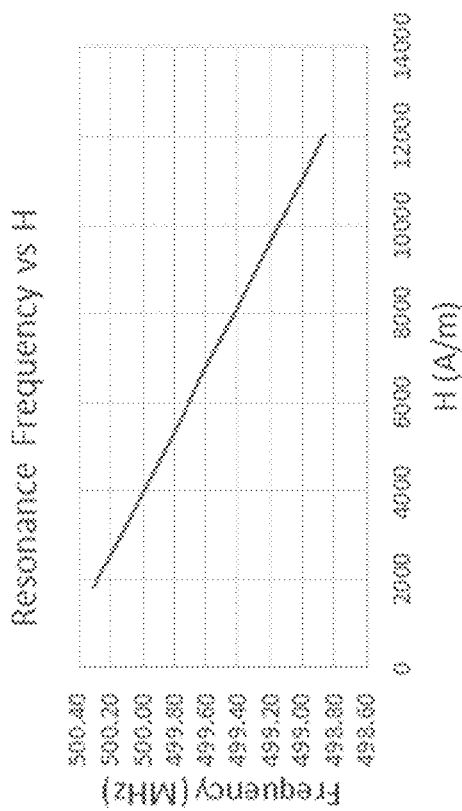
FIG. 17 illustrates an exemplary resonance frequency shift, for the embodiment of FIG. 15, as a function of the magnetic field.

FIG. 17 illustrates an exemplary resonance frequency shift for the embodiment of FIG. 15, as a function of the magnetic field. In this example, magnetic beads (for example as those described by Fannin referenced above) are deposited over an LC oscillator with a base inductor value L0 of 17 nH and a capacitance of 5.9 pF. The inductance variation as a function of the magnetic field will be $\Delta L/\Delta H=9.7$ fH/(A/m), giving a variation of the frequency as a function of the magnetic field of $\Delta f/\Delta H=141$ Hz/(A/m). For an exemplary requirement of 1 mm spatial resolution to distinguish adjacent microsensors, and a gradient for the magnetic field of 30 mT/m, a variation of $\Delta H=24$ A/m will give a variation in the resonance frequency $\Delta f=3.4$ kHz.

The above example is intended to give exemplary values for the quantities involved in the device and methods of the present disclosure. The person skilled in the art will understand that different values may be used, depending on the requirements of a specific application.

Figure 18:
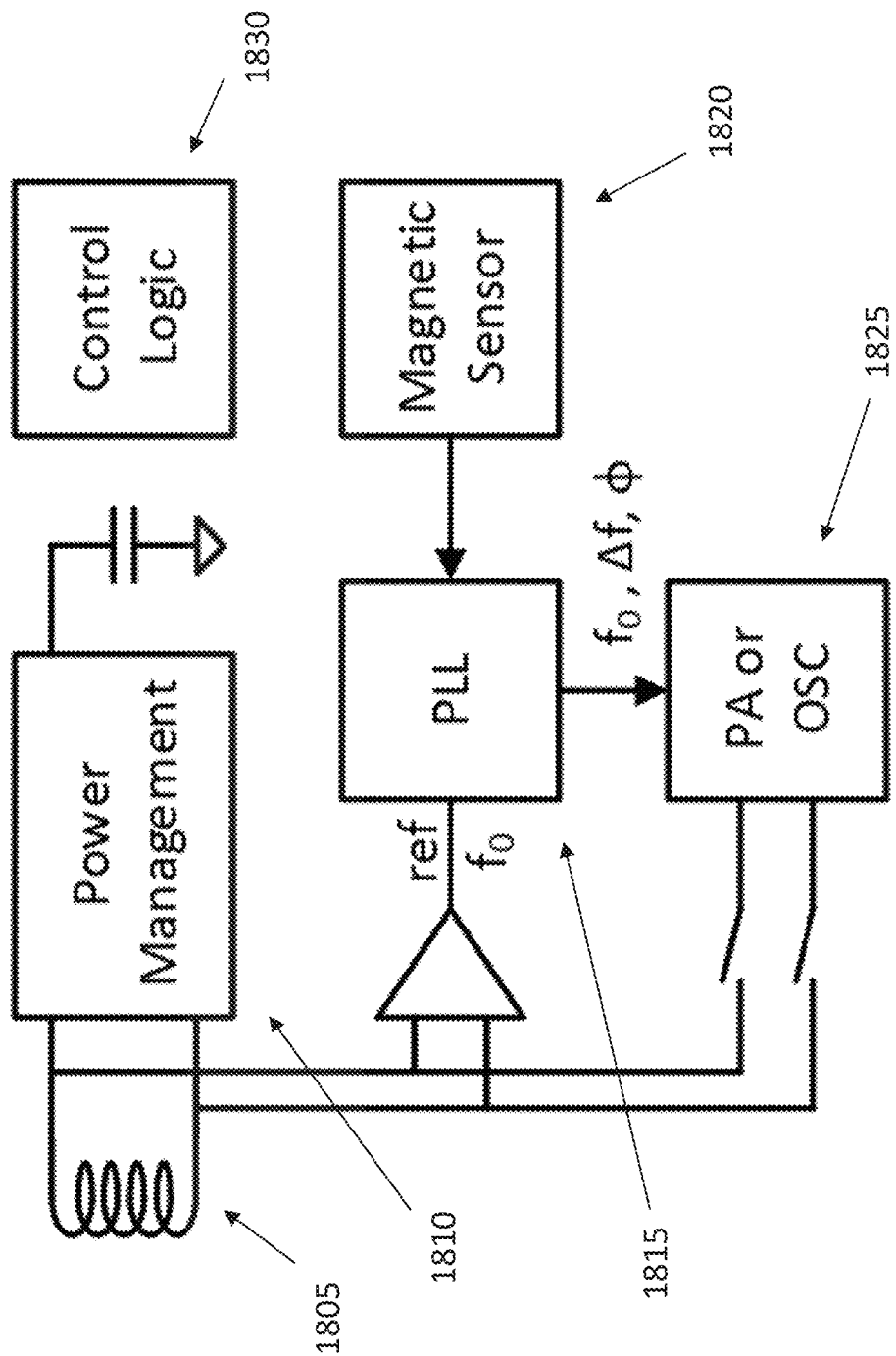
FIG. 18 illustrates an exemplary system architecture of ATOMS.

FIG. 18 illustrates an exemplary system architecture of ATOMS. A microcoil (1805) can be used to interface with RF magnetic fields. The power management unit (1810) can harvest energy from the RF fields to power all of the IC's functions, including sensing and actuation of biological processes. A phase-locked loop (PLL, 1815) can be used to acquire the frequency and phase of the existent RF magnetic field. When more than one device is used, the PLL (1815) allows synchronization of multiple ATOMS in frequency and phase. The magnetic sensor (1820) measures the magnetic field gradient and can be used to produce a frequency shift or phase shift. The power amplifier (PA, 1825) can be used to drive the microcoil (1805) and transmit the modified RF signal ($f_0+\Delta f/\Delta\phi$), according to the methods explained in the disclosure herein. The control logic (1830) manages the operation of the whole device, including calibration and adaptation. The microcoil/antenna (1805) can be either designed to be on-chip or off-chip.

Figure 19:
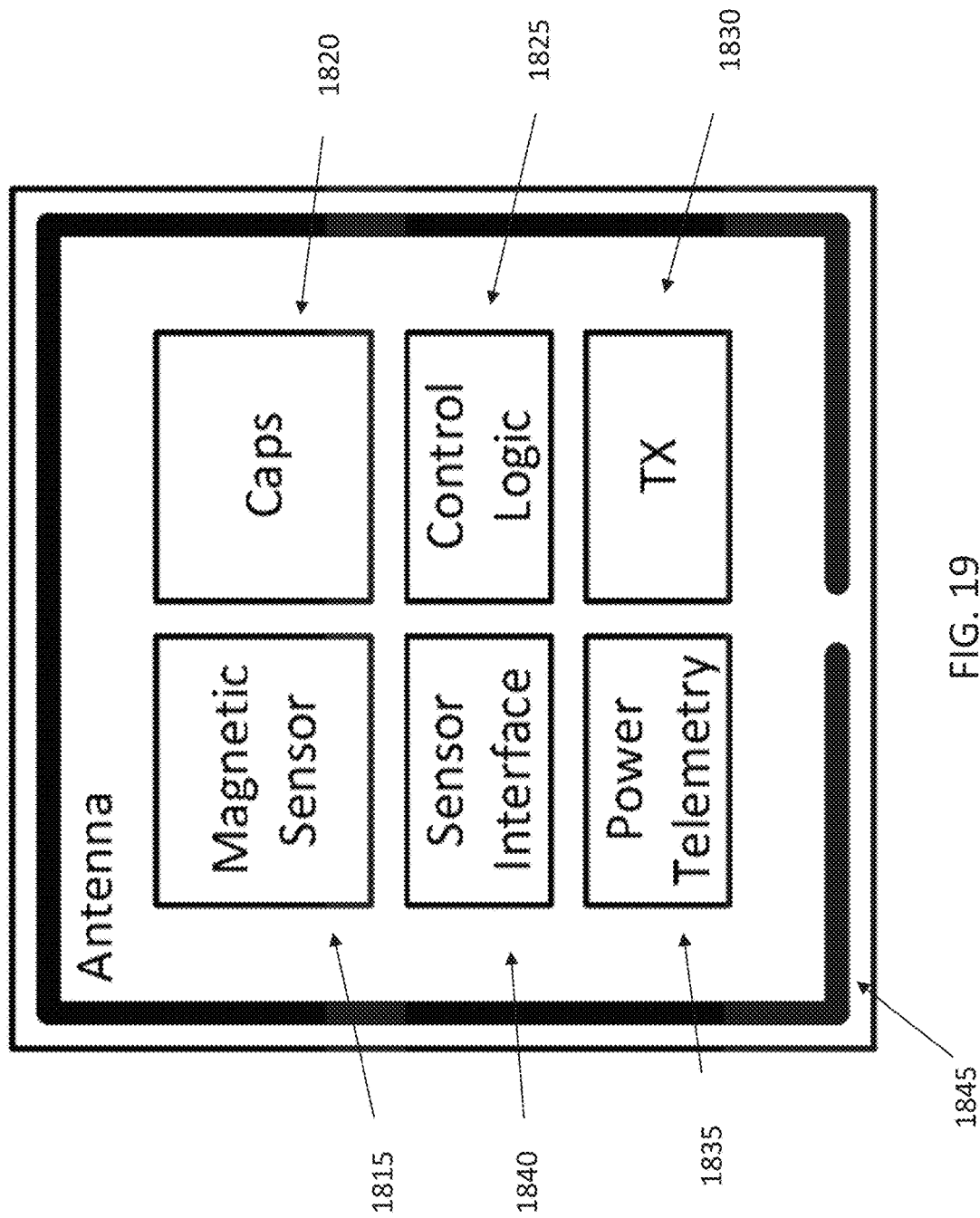
FIG. 19 illustrates an exemplary chip and antenna of a microsensor.

FIG. 19 illustrates an exemplary chip and antenna of a microsensor. In the present disclosure, a microsensor may refer to the whole sensing device, or to the specific component within the device which is actually able to sense a physical, biological or chemical quantity.

For example, the microsensors may comprise a magnetic sensor (1815), capacitors (1820), a control logic circuit (1825), a transmitter/receiver module (1830), a circuit to handle power and telemetry (1835), a sensor interface (1840), and an antenna (1845). For example, the antenna (1845) may comprise a strip of metal running around the majority of the microsensor's boundary.

To produce a frequency shift, the PLL can be modified to allow a variation of its operation frequency during transmission. For this purpose, an additional MOS varactor can be used to modify the oscillation frequency.

Another method to produce a frequency shift is through injection locking. This allows a low power and fast locking system with a simple implementation. In addition, it allows for deskew which can be used for phase encoding.

To produce a phase shift, injection locking can be used as disclosed herein. A phase interpolator can also be used to produce a phase shift. Another method is by adding a controllable delay stage at the output of the voltage controlled oscillator (VCO).

To minimize the area of the chip on which the microsensors are fabricated, the analog circuits can be designed and optimized to enable both oscillation and transmission to happen via a single inductor/antenna. In some embodiments, the optimum frequency of transmission can be determined considering factors such as tissue absorption, available area, sensitivity of the external system and maximum harvested power. Both near-field and far-field transmission modes can be considered and carefully modeled.

In some embodiments, the design can take into account additional factors such as efficiency of on-chip power harvesting and power management. In some embodiments, a time-multiplexed scheme can be used, where a power-harvesting phase is followed by a sensing and transmission phase. Such a scheme allows the use of the same inductor used in the transmission as a secondary coil during the power harvesting from the radio frequency (RF) signal. Such an approach can be viable if sensing and transmission require energy levels that can be stored in on-chip capacitors. Therefore, it may be advantageous to design ultra-low-power mixed-signal circuits for sensing and efficient analog circuits for signal transmission.

Another method is to have a separate dedicated transmitter to provide RF signal at a different frequency for constant power transmission. Yet another method is to use backscattering for communication. This method might be more suitable for implants that are close to the body surface.

More sophisticated communication methods can be carried out, similarly to more elaborated MRI coding sequences. A calibration phase to set the resonance frequency of ATOMS can be required.

The magnetic sensor can be on-chip or off-chip. On-chip sensors compatible with standard CMOS technologies can be limited to Hall-effect sensors. Off-chip sensors can use paramagnetic materials, flux-gates, giant-magnetoresistors (GMR).

Three-dimensional (3D) magnetic sensors can also be used. An on-chip 3D magnetic sensor can use one horizontal Hall-plate and two orthogonal vertical Hall-plates. A method to obtain 3D localization of ATOMS with unknown orientation can involve the utilization of a 3D magnetic sensor and adding temporal information as a fourth dimension.

Another method is to use multiple on-chip sensors placed at different locations. For example, the 3D sensors can be placed in the corners of the chip to measure the orientation.

Another method is to use a self-aligning sensor. For example, paramagnetic materials (thin-films and magnetic beads) can align their magnetization field to an external magnetic field like nuclei in an MRI. Thus, ATOMS with unknown orientation can have a magnetic sensor that aligns itself to the external magnetic field.

Figure 20:
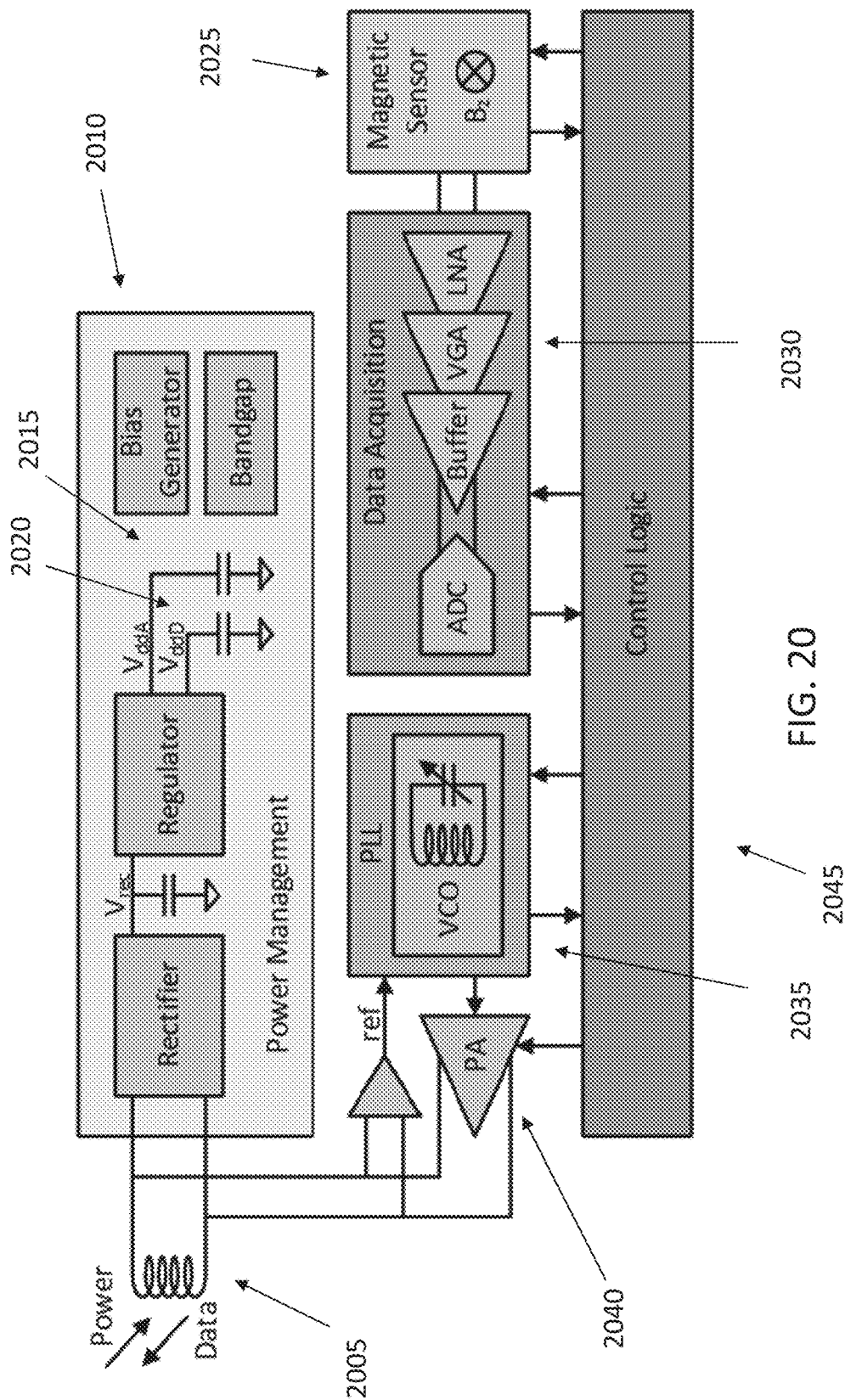
FIG. 20 illustrates a detailed exemplary system architecture of a microsensor.

FIG. 20 illustrates a detailed exemplary system architecture of a microsensor. A single microcoil (2005) can be used to receive power and communicate with the external system. The power management unit (2010) can generate the internal power supplies for analog circuits (2015, $V_{ddA}$) and digital circuits (2020, $V_{ddD}$) to power the chip. The magnetic sensor (2025) can measure the magnetic field and its output can be amplified and digitized by the data acquisition unit (2030). The PLL (2035) acquires the frequency and phase of the existent RF magnetic field and uses the data generated by the data acquisition unit (2030) to produce a frequency shift or phase shift. Then, the output of the PLL (2035) is sent to the power amplifier (2040, PA) to drive the antenna (2005) and communicate with the external system. The operation of the whole device is managed by the control logic (2045). The different blocks of the system architecture shown in FIG. 20 are explained further herein.

Figure 21:
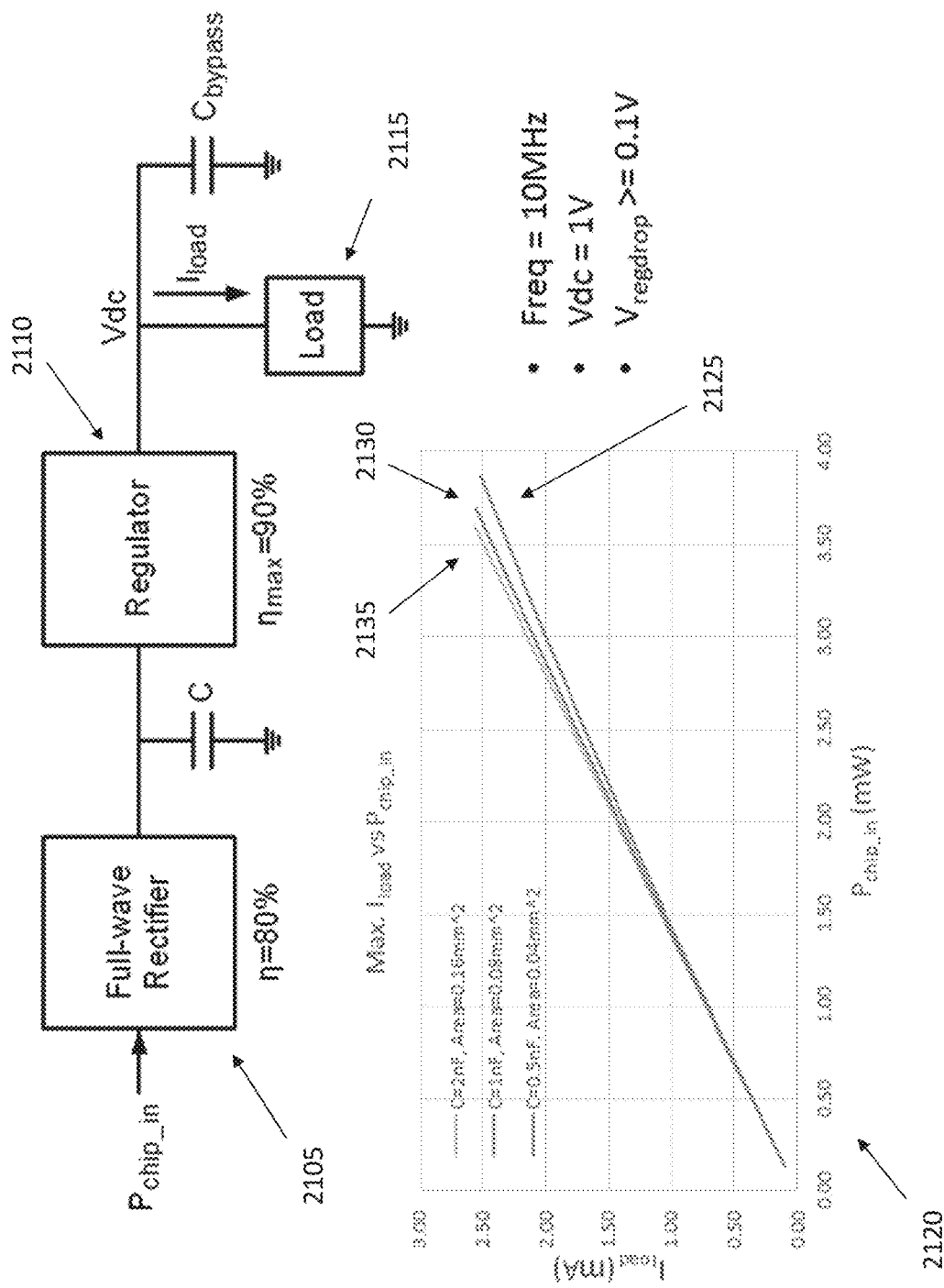
FIG. 21 illustrates an exemplary power harvesting circuit for a microsensor.

FIG. 21 illustrates an exemplary power harvesting circuit for a microsensor. A full wave rectifier (2105) receives power and produces a rectified voltage that goes to the voltage regulator (2110) and then applied to a load (2115). For example, the frequency of the current could be 10 MHz, with a direct current voltage of 1 V and a regulator drop of 0.1 V or more. An exemplary max load current is plotted (2120) in FIG. 21 versus the power received by the rectifier, for three different capacitances: C=2 nF, area of 0.16 squared millimeters (2135); C=1 nF, area of 0.08 squared millimeters (2130); C=0.5 nF, area of 0.04 squared millimeters (3125).

Figure 22:
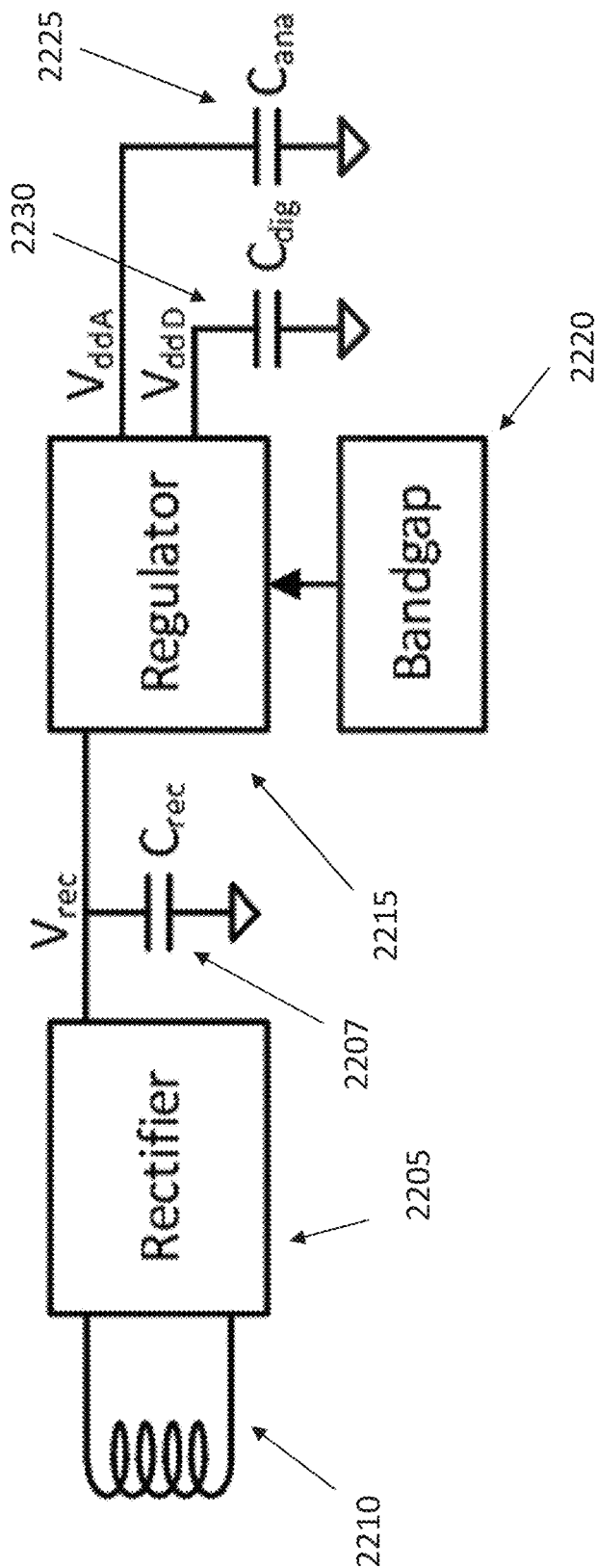
FIG. 22 illustrates a more detailed exemplary power management circuit.

FIG. 22 illustrates a more detailed exemplary power management circuit. A full-wave rectifier (2205) is connected to the antenna (2210). A capacitor $C_{rec}$ (2207) is connected to the output of the rectifier (2205) to produce the rectified voltage $V_{rec}$. The regulator (2217) uses this signal along with the output of a voltage bandgap circuit (2220) and two capacitors $C_{ana}$ (2225) and $C_{dig}$ (2230) to produce two power supplies $V_{ddA}$ and $V_{ddD}$ to power the analog circuits and digital circuits, respectively.

Figure 23:
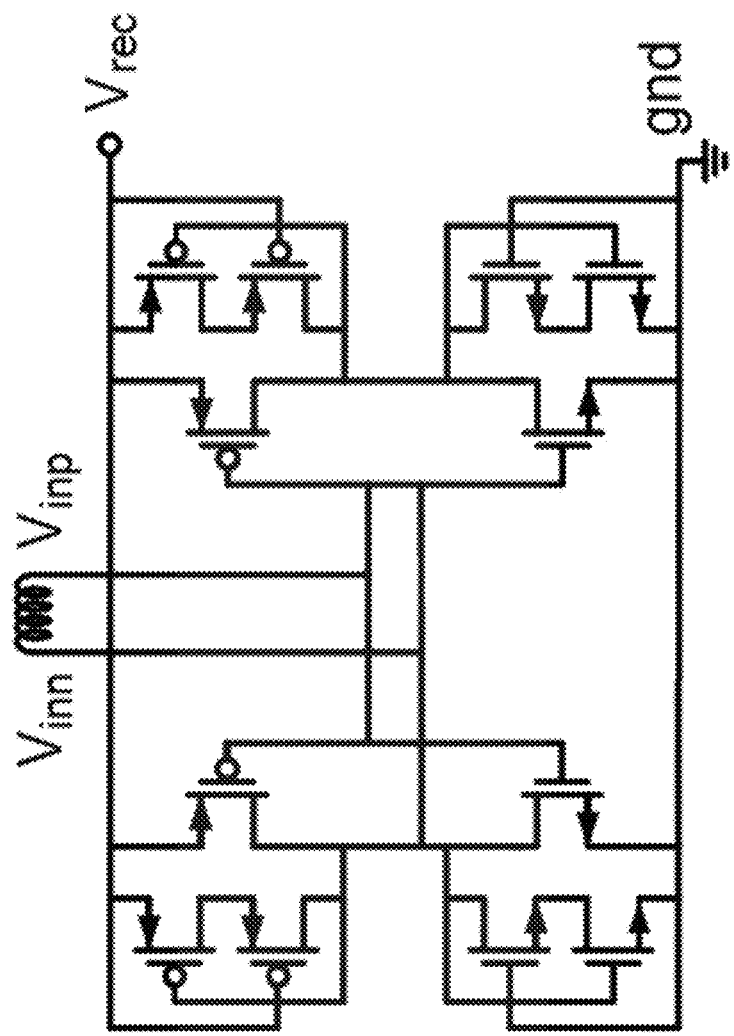
FIG. 23 illustrates the electrical circuit schematic of the rectifier.

FIG. 23 illustrates an exemplary electrical circuit schematic of the rectifier of FIG. 22. A self-synchronous rectifier may be used for this stage. The power transistors can include dynamic body biasing.

Figure 24:
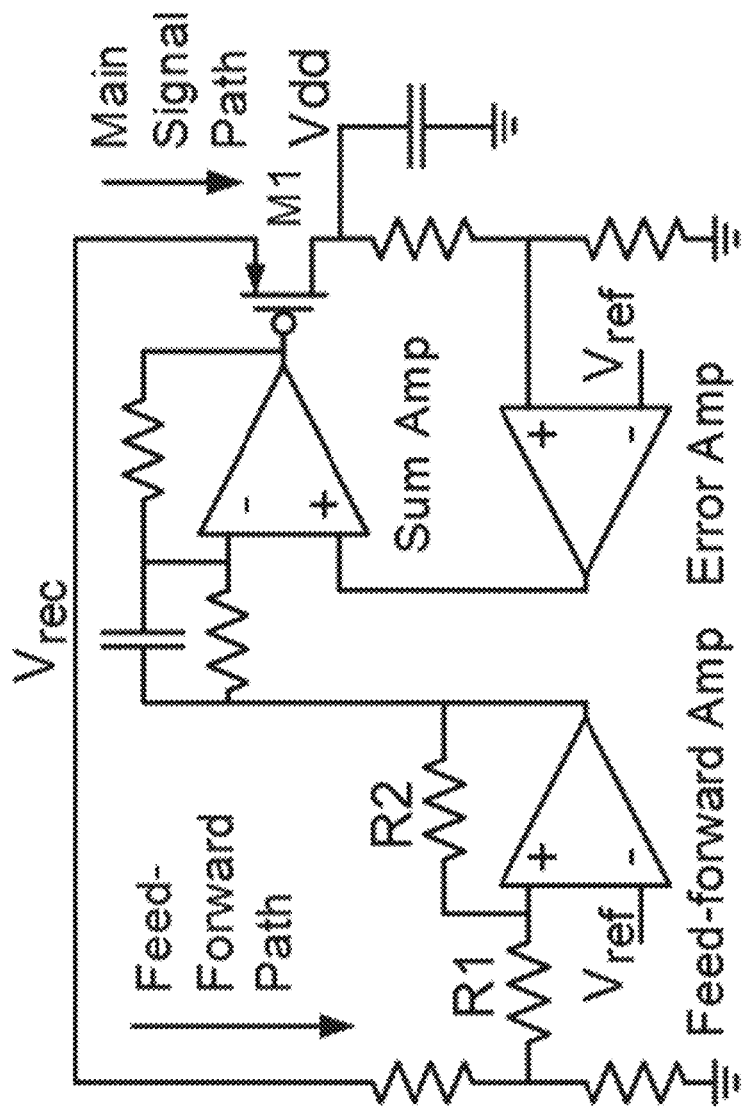
FIG. 24 illustrates the electrical circuit schematic of the analog regulator.

FIG. 24 illustrates an exemplary electrical circuit schematic of the analog regulator of FIG. 22. A feed-forward ripple-cancellation scheme can be used in this stage. In this scheme, the input ripples are filtered out by replicating the same ripples at the gate of transistor M1 through a feed-forward path. This technique produces a high power supply rejection ratio (PSRR) and also increases its bandwidth by the addition of a zero in the summing amplifier (Sum Amp).

Figure 25:
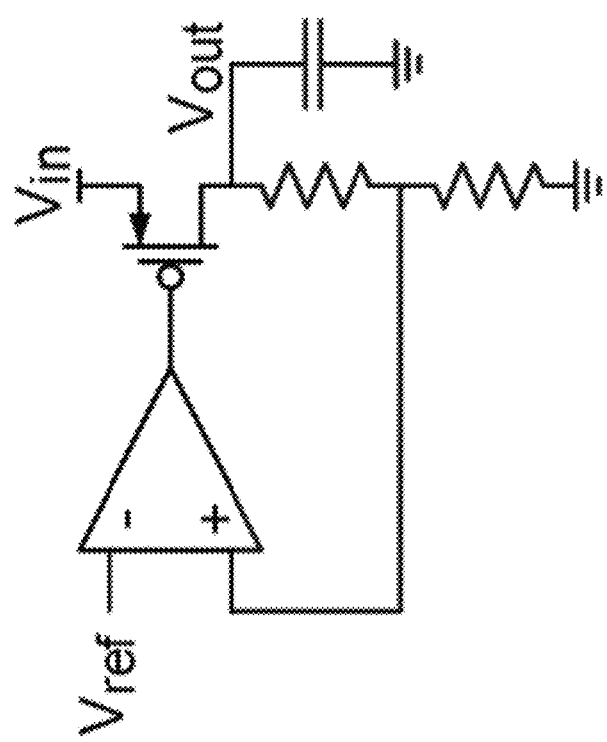
FIG. 25 illustrates the electrical circuit schematic of the digital regulator.

FIG. 25 illustrates an exemplary electrical circuit schematic of the digital regulator of FIG. 22. For this stage, a traditional regulator can be used since digital circuits are more tolerant of noise in the power supply. In addition, this stage has lower power consumption with respect to the feed-forward scheme described herein.

Figure 26:
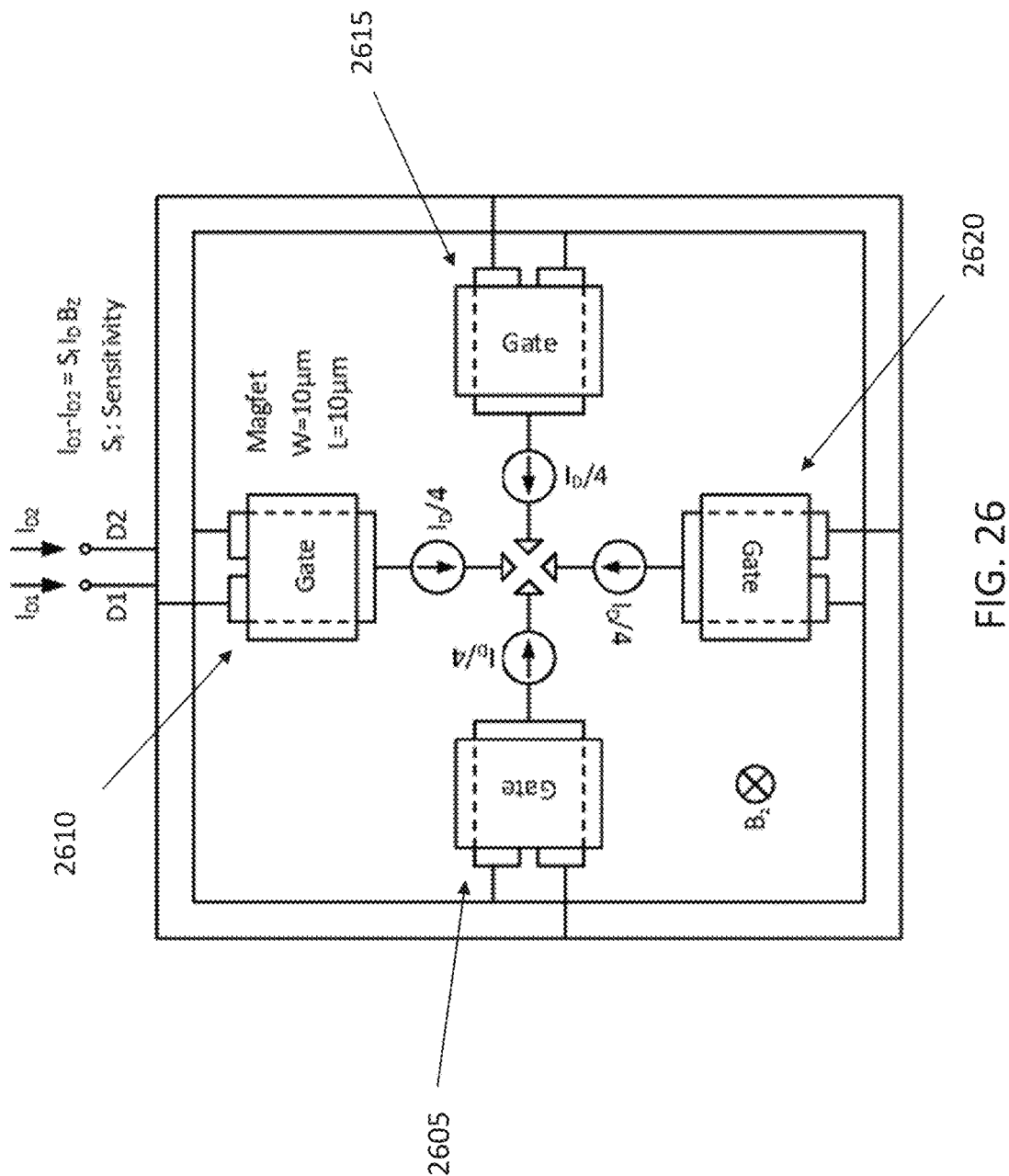
FIG. 26 illustrates an exemplary schematic of a magnetic sensor.

FIG. 26 illustrates an exemplary schematic of the magnetic sensor of FIG. 20. In this circuit, four MAGFET connected in parallel are used (2605, 2610, 2615, 2620). To reduce the offset of the sensor, a common-centroid structure can be used, where each MAGFET is facing north, south, east and west, respectively. In addition, individual P-wells can be used to cancel the body effect. For example, each MAGFET can be a device with a width of 10 μm and a length of 10 μm, and a behavior as described above in the present disclosure.

Figure 27:
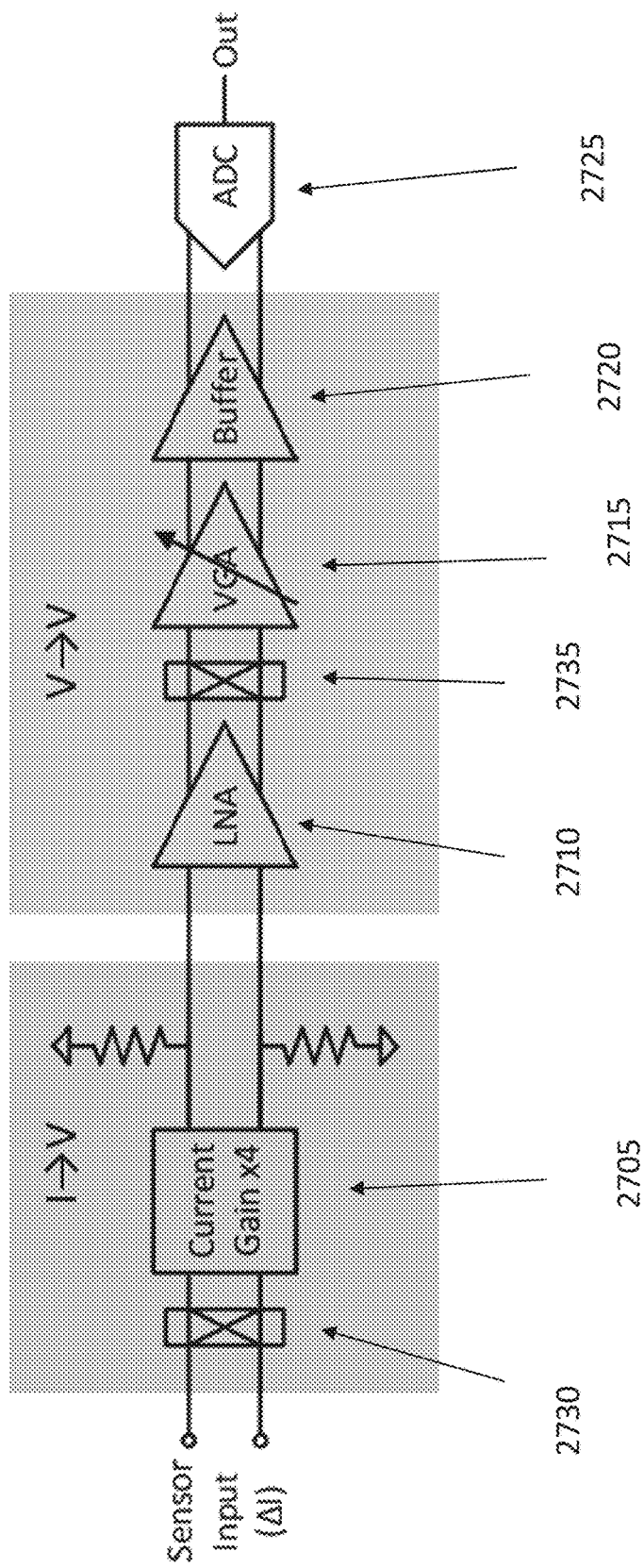
FIG. 27 illustrates an exemplary circuit schematic of the data acquisition unit.

FIG. 27 illustrates an exemplary circuit schematic of the data acquisition unit of FIG. 20. A transimpedance amplifier (2705) can be used to amplify the output of the magnetic sensor to microvolts levels. A low-noise amplifier (LNA, 2710) followed by a variable-gain amplifier (VGA, 2715) can be used to then amplify the signal to millivolts levels. A buffer (2720) can be used to drive the analog-to-digital converter (2725) that digitizes the amplified signal.

A chopper technique can be used to minimize the flicker noise (1/f noise). The chopper switches (2730, 2735) can be added at the input of the stage of FIG. 27, before the transimpedance amplifier (2705) and after the LNA (2710). To minimize the power consumption, a low-voltage design (sub-1V design) with digital self-calibration can be used.

Figure 28:
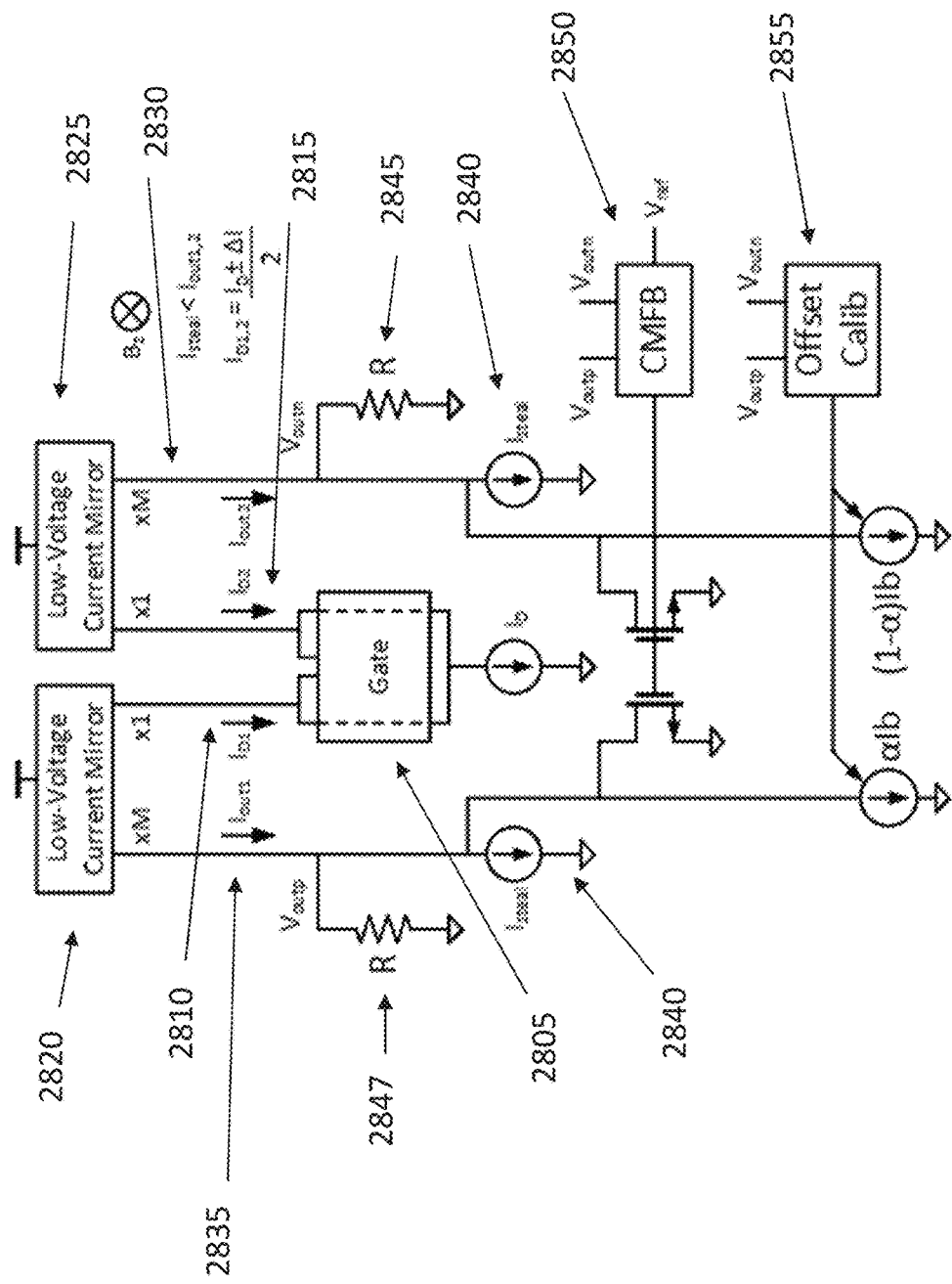
FIG. 28 illustrates an exemplary circuit schematic of the transimpedance amplifier.

FIG. 28 illustrates the circuit schematic of the transimpedance amplifier of FIG. 27. The MAGFET (2805) in the center represents the four MAGFET structure described above in FIG. 26. That is, the sensor can be built with different numbers of MAGFET that can be linked in parallel. For example, the MAGFET of FIG. 28 could be a single MAGFET, or it could by a symbol representing the four MAGFETs connected in parallel as described in FIG. 26, or it could represent a different number of MAGFETs. The outputs of the MAGFET (2805) are the drain currents $I_{D1}$ (2810) and $I_{D2}$ (2815). Both of these currents (2810, 2815) are amplified by a low-voltage current mirror (2820, 2825) by a factor of M. The outputs of the current mirrors (2820, 2825) are $I_{out1}$ (2835) and $I_{out2}$ (2830), respectively. Because the output of the magnetic sensor is a very small signal added to a much bigger bias current, most of this bias current is removed by current sources $I_{steal}$ (2840). This current $I_{steal}$ (2840) is designed to be less than the output currents $I_{out1}$ (2835) and $I_{out2}$ (2830) to guarantee no information loss. The difference currents $I_{out1}-I_{steal}$ and $I_{out2}-I_{steal}$ then flow to matched resistors R to generate the differential output $V_{outp}$ (2847) and $V_{outn}$ (2845), respectively.

A common-mode feedback (CMFB) circuit (2850) can be added to ensure that the output common-mode voltage is correct. Similarly, a differential offset calibration circuit (2855) can be added to minimize the offset of the transimpedance amplifier and any offset produced by the MAGFET (2805). For example, the Earth's magnetic field generates an offset in the MAGFET (2805) that has to be cancelled.

Figure 29:
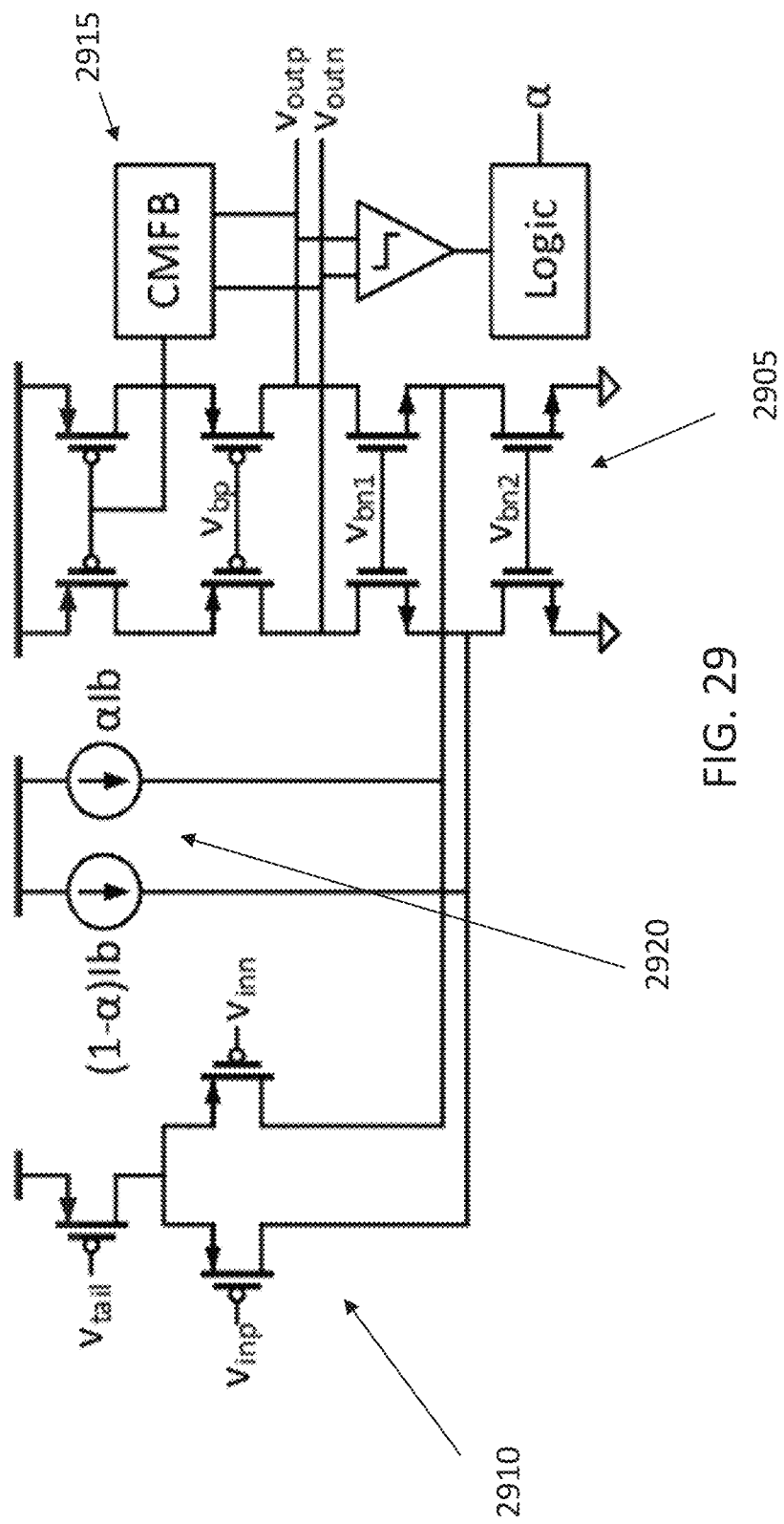
FIG. 29 illustrates an exemplary circuit schematic of the LNA.

FIG. 29 illustrates the circuit schematic of the LNA of FIG. 27. A fully differential folded cascade stage (2905) can be used. The differential transistor pair (2910) at the input can be biased in weak inversion to provide a high gain-noise-power efficiency. To improve the power efficiency even further, a low-voltage design with offset calibration can be adopted. A CMFB (2915) can be added to ensure that the output common-mode voltage is correct. For example, the gain of this stage can be higher than 50 dB with a bandwidth of 10 kHz, and an input referred voltage noise density of this stage can be 160.5 nV/sqrt(Hz) at 1 kHz.

A self-calibration offset cancellation scheme can comprise a digital comparator connected at the output of the LNA to sense its offset and a differential current source (2920) to minimize the offset. This differential current source injects current at a low-impedance node, minimizing gain reduction. The control logic uses the information taken by the comparator to adjust the differential current source to the desired setting, in a self-calibration fashion. The differential current source can be implemented using a differential current digital-to-analog converter (DAC).

Figure 30:
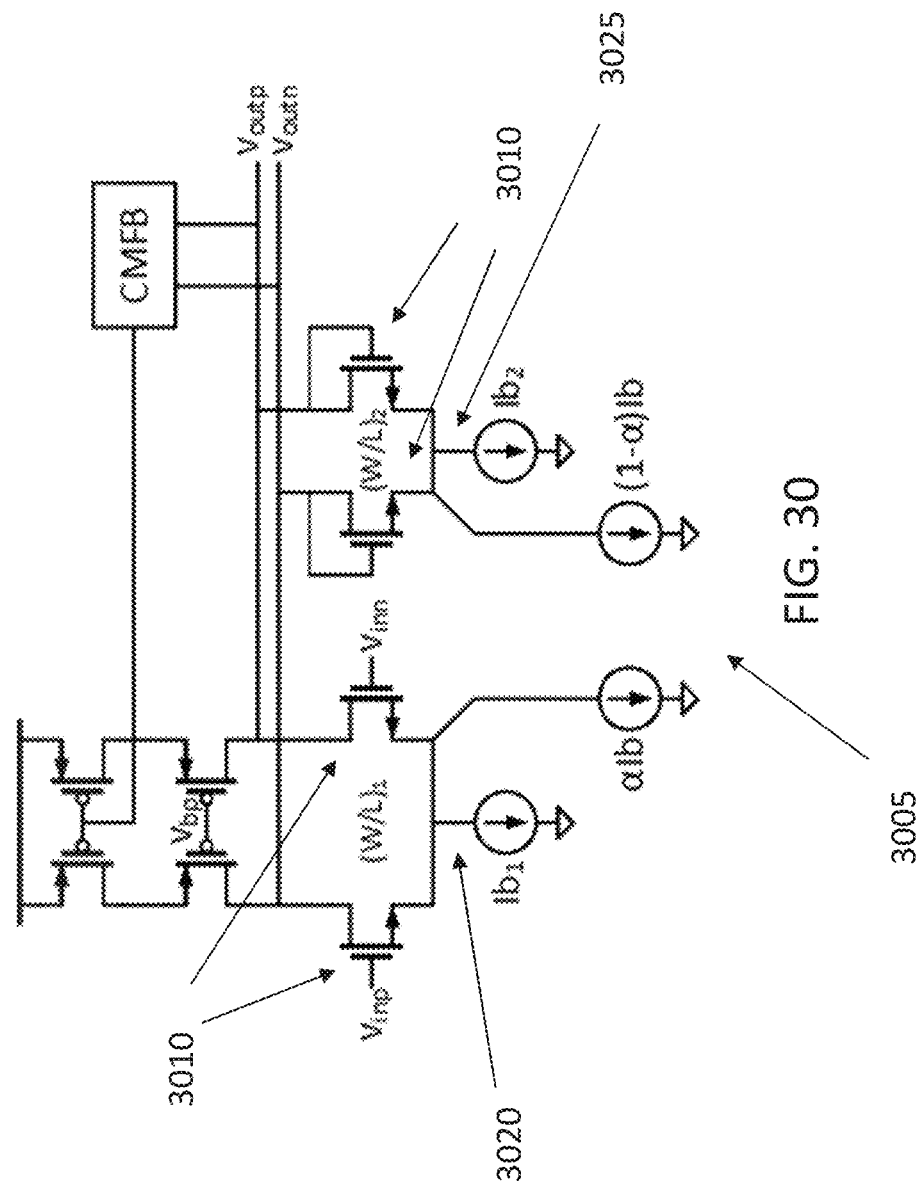
FIG. 30 illustrates an exemplary circuit schematic of the VGA.

FIG. 30 illustrates an exemplary circuit schematic of the VGA of FIG. 27. In this stage, an N-type MOS (NMOS) differential transistor pair with NMOS load can be used. This arrangement allows gain control through the bias currents. In this stage, a differential current source (3005) can be added to control the gain and to improve gain linearity in the dB-range. The differential current source (3005) can be implemented using a differential current DAC. For example, this stage can have a gain variation from 1 dB to 20 dB, and a bandwidth of 100 kHz.

The gain of the VGA of FIG. 30 depends on the form-factor of matched input transistors (3010), the form-factor of matched load transistors (3015) and bias currents for input (3020) and load (3025) transistors. Current sources $\alpha I_b$ and $(1-\alpha)I_b$ can be implemented using a differential current DAC, where α is the digital input that controls the gain. The form-factor of matched input transistors (3010) has a size of $(W/L)_1$. The form-factor of matched load transistors (3015) has a size of $(W/L)_2$. The bias current for the input transistor (3020) is $I_{b1}+\alpha I_b$ and the bias current for the load transistor (3025) is $I_{b2}+(1-\alpha)I_b$. The equation below gives a mathematical expression for the gain of the VGA of FIG. 30.

$$A_v = \sqrt{\frac{(W/L)_1}{(W/L)_2} \frac{I_{b1} + \alpha I_b}{I_{b2} + (1-\alpha)I_b}}$$

Figure 31:
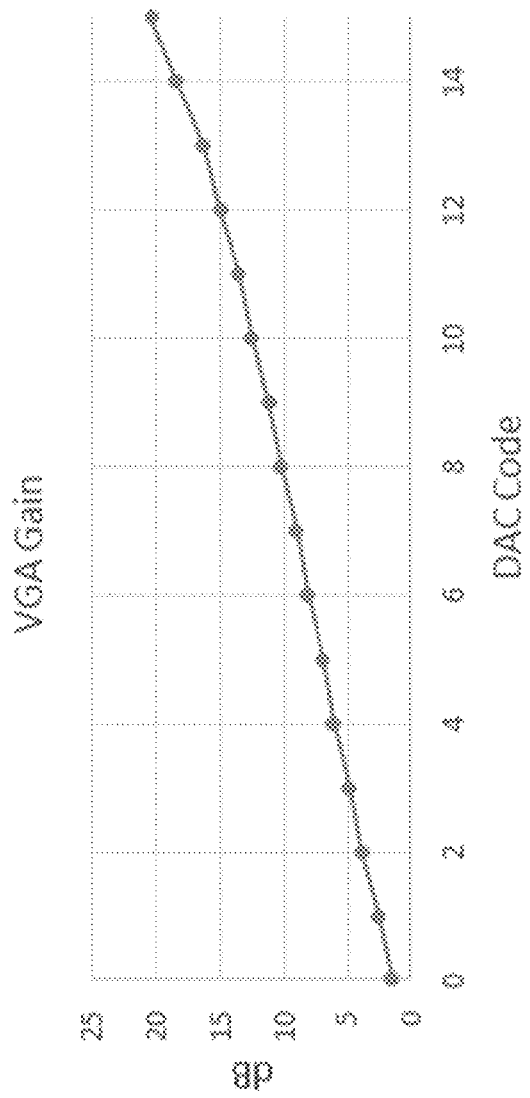
FIG. 31 illustrates exemplary simulation results of the VGA in FIG. 30.

FIG. 31 illustrates exemplary simulation results of the VGA in FIG. 30.

The design of the PLL can be challenging because of the requirements of ATOMS. The target frequency range is much smaller than that of traditional applications. In addition, the PLL has to keep the oscillation frequency without the reference signal.

To adjust the frequency range of the PLL to the target range, a low gain VCO can be used. The gain of the VCO is defined as $K_{VCO}$, which relates the output oscillation frequency to its input voltage ($V_{ctrl}$). By adopting a low $K_{VCO}$ design, not only the frequency range of the PLL can be reduced, but the PLL is also made less sensitive to variations in $V_{ctrl}$.

Another effect of having a low $K_{VCO}$ is that it can make the PLL more susceptible to variations in the fabrication process. Taking this into consideration, a digital course tuning can correct for process variation. A digital control logic can calibrate the PLL to bring the frequency range to the target range. A separate analog fine tuning input in the VCO can lock the PLL to the input signal.

Because the PLL needs to keep the oscillation in the absence of a reference signal, an oscillation detector can be added. The absence of the reference signal can be seen as a very low frequency signal by the PLL, which will then try to adjust the frequency of the output signal to follow the reference. This behavior of the circuit is not desired. Thus, the oscillation detector allows the PLL to open its feedback loop and stop any miscorrection caused by the absence of the reference signal.

Figure 32:
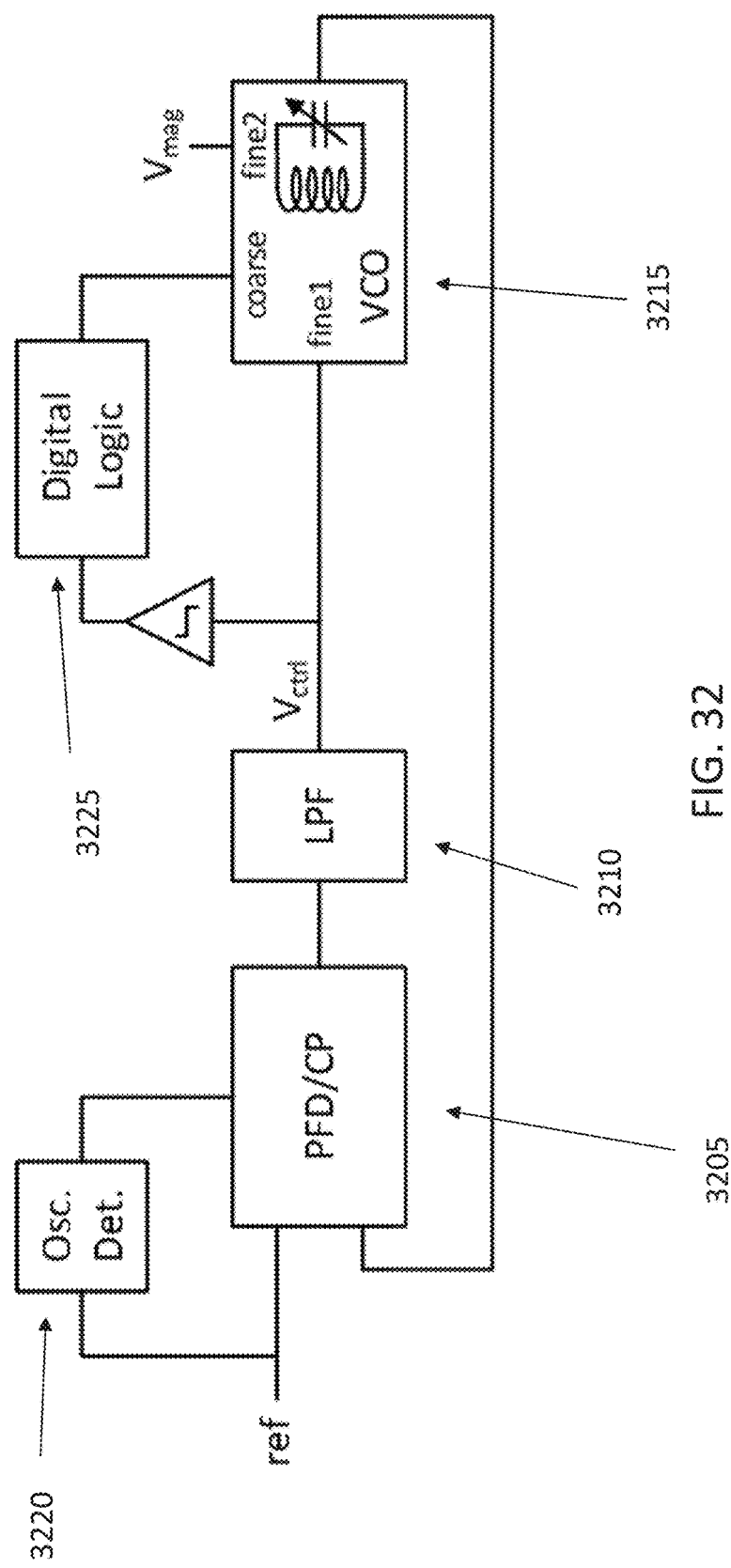
FIG. 32 illustrates an exemplary circuit schematic of the PLL.

FIG. 32 illustrates an exemplary circuit schematic of the PLL of FIG. 20. The PLL comprises a phase-and-frequency detector (PFD) and a charge-pump (CP) module (3205), a low-pass filter (LPF, 3210), a VCO (3215), an oscillator detector (Osc. Det., 3220), a comparator and a digital control logic (3225) for self-calibration. The VCO (3215) can have an additional analog input to generate frequency shifts.

Figure 33:
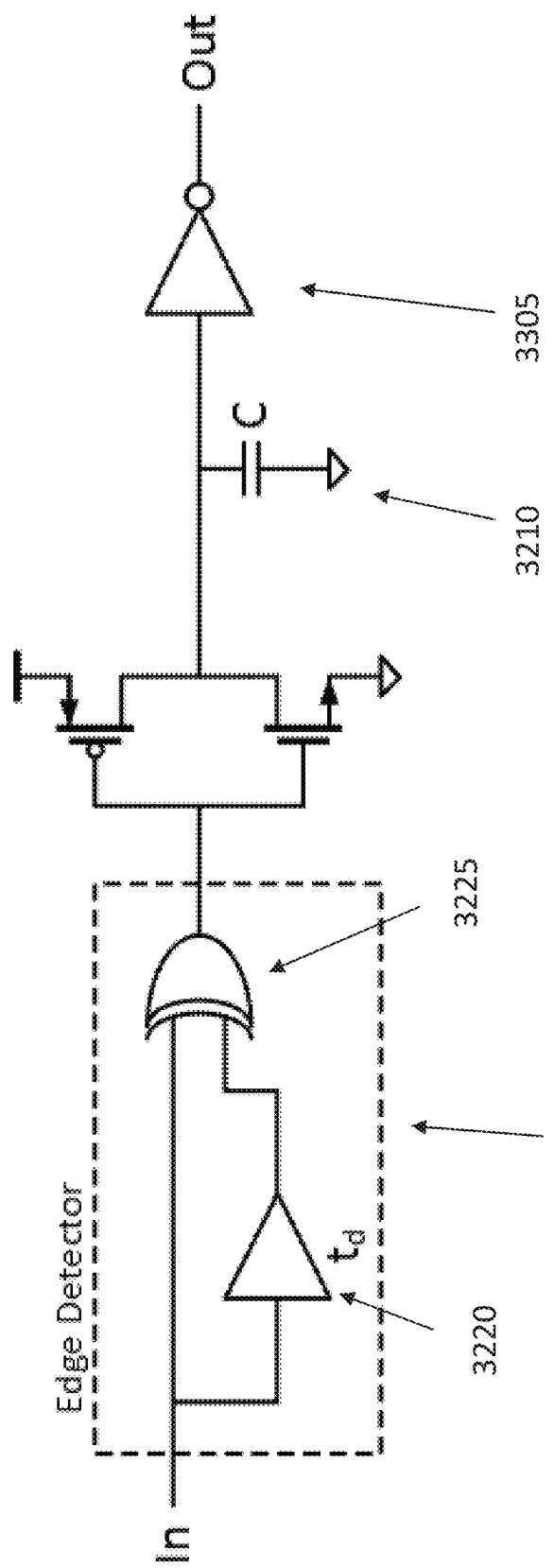
FIG. 33 illustrates an exemplary circuit schematic of the oscillator detector.

FIG. 33 illustrates an exemplary circuit schematic of the oscillator detector of FIG. 32. In some embodiments, a customized inverter (3205) with a capacitor C (3210) with a fast falling time and a slow rising time tuned for the target frequency range can be used. This circuit is connected to the output of the edge detector (3215), which will reset the capacitor C (3210) every half a period. The edge detector can be implemented using a delay stage (3220) and an OR-exclusive digital gate (XOR, 3225).

When the reference signal is present, the output of the customized inverter does not have enough time to increase above the threshold voltage of the followed inverter. Thus, the output of this inverter does not change, and the output of the oscillator detector is equal to one (digital one). When there is no reference, the output of the customized inverter has enough time to rise above the threshold value, changing the output of the oscillator detector to zero (digital zero).

In order to detect oscillations at a given frequency, there has to be a waiting time of at least half of the period of the oscillation. This step has to be taken into account because its omission can cause a miscorrection step in the PLL. To avoid this miscorrection, the PLL can keep tract of the input of the VCO ($V_{ctrl}$). When there is no reference signal, if such a miscorrection happens, the control logic can update the wrong value of $V_{ctrl}$ with the value previously recorded.

Figure 34:
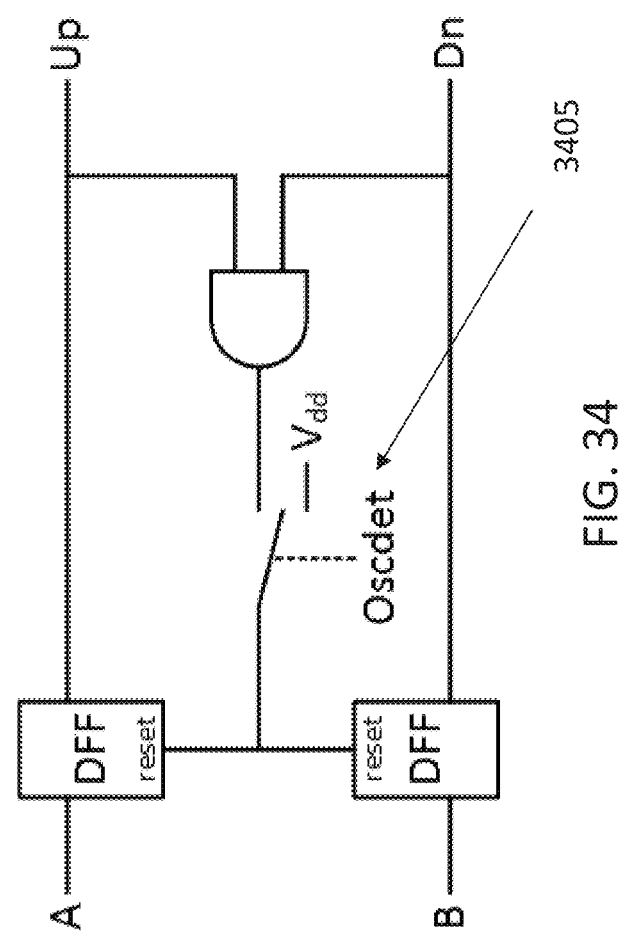
FIG. 34 illustrates an exemplary circuit schematic of the PFD.

FIG. 34 illustrates an exemplary circuit schematic of the PFD of FIG. 32. A flip-flop with NAND digital gate, known to the person skilled in the art, can be used. The oscillation detector output, termed oscdet, (3405) can be used to open the feedback loop of the PFD when there is no reference signal.

Figure 35:
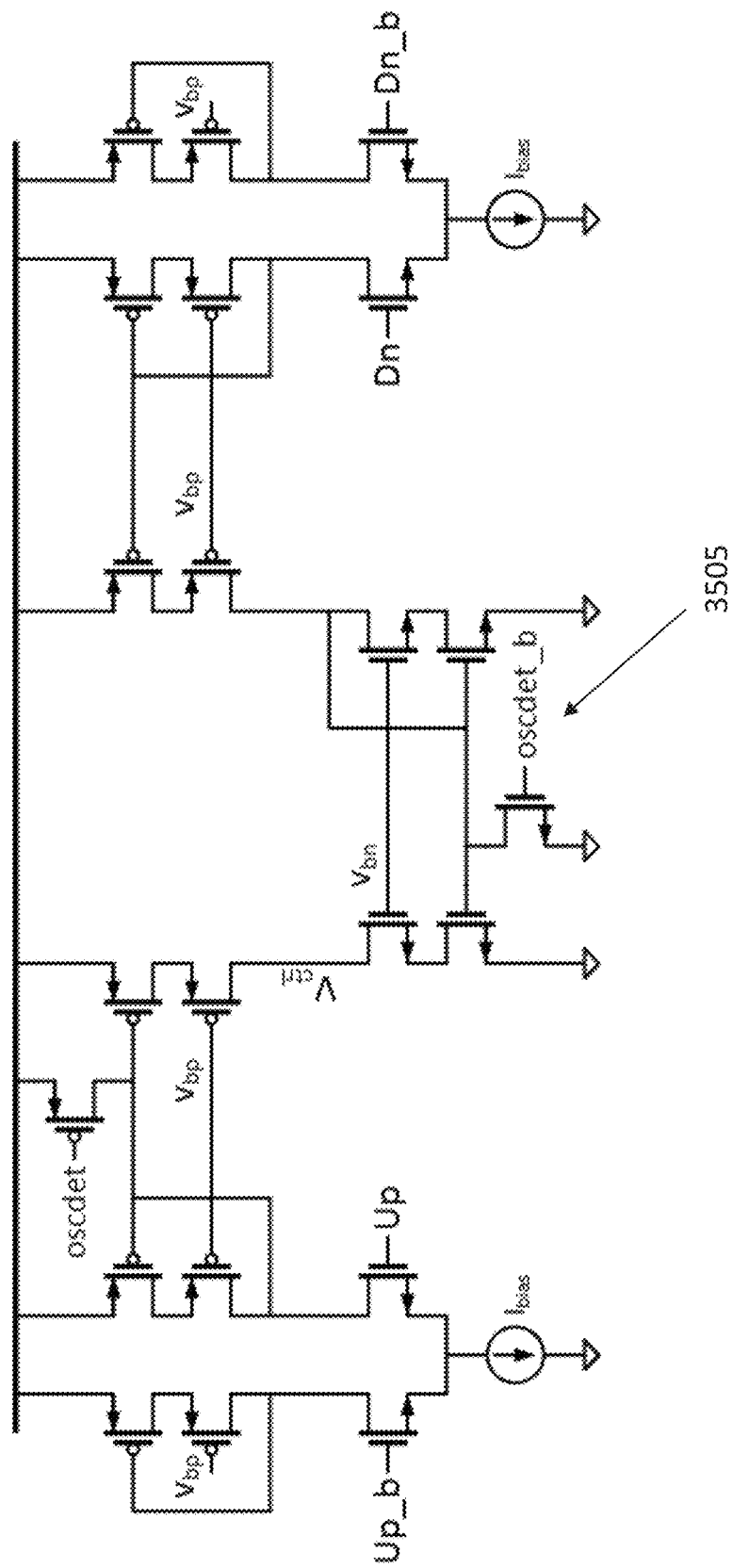
FIG. 35 illustrates an exemplary circuit schematic of the CP.

FIG. 35 illustrates an exemplary circuit schematic of the CP of FIG. 32. A differential stage DP can be used. The oscillation detector outpu5, termed oscdet, (3505) can be used to open the output of the CP when there is no reference signal.

Figure 36:
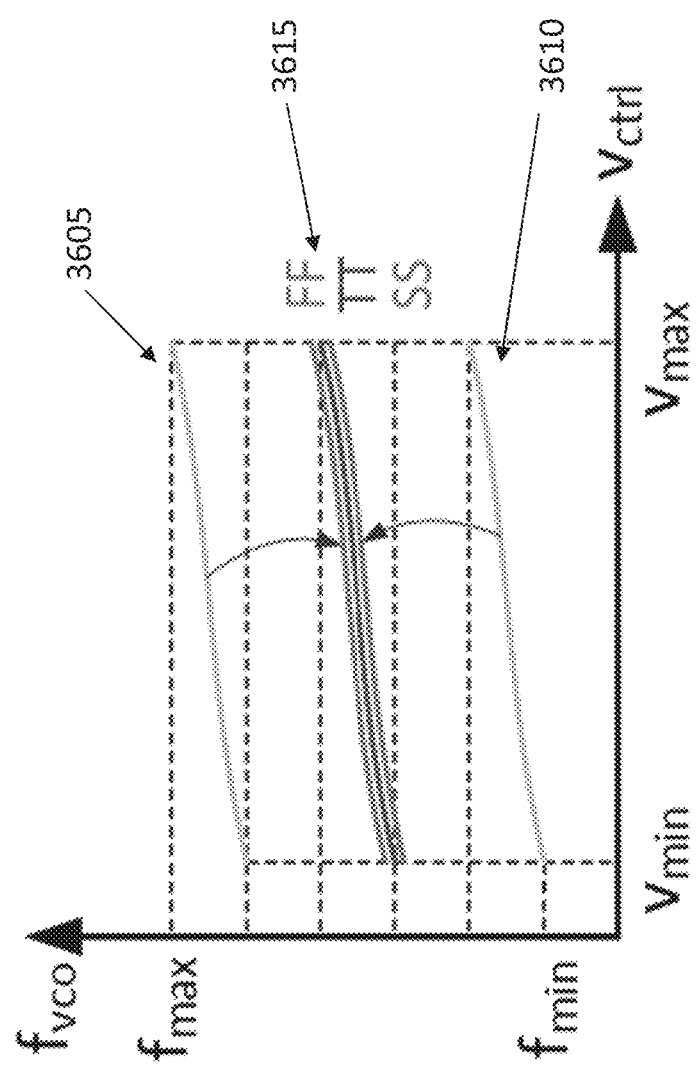
FIG. 36 illustrates an exemplary diagram showing the effect of the digital calibration.

FIG. 36 illustrates an exemplary diagram showing the effect of the digital calibration. Due to variations in the fabrication process, the frequency range of the VCO can be out of the target range. For example, in one case (3605) the frequency can be above the target range and in another case (3610) the frequency can be below the target range. By adding a digital calibration loop, the PLL can bring out-of-target cases (3605, 3610) close to the typical case (3615) and to the target range. This calibration is done automatically, in a self-calibration fashion.

An example of this self-calibration process is described in the following. By opening the PLL loop and integration over time, the output of the PFD/CP/LPF ($V_{ctrl}$) provides the information for the calibration. With an open loop, $V_{ctrl}$ saturates to VDD or GND indicating that the output frequency of the PLL is either higher or lower than the frequency of the reference signal.

Figure 37:
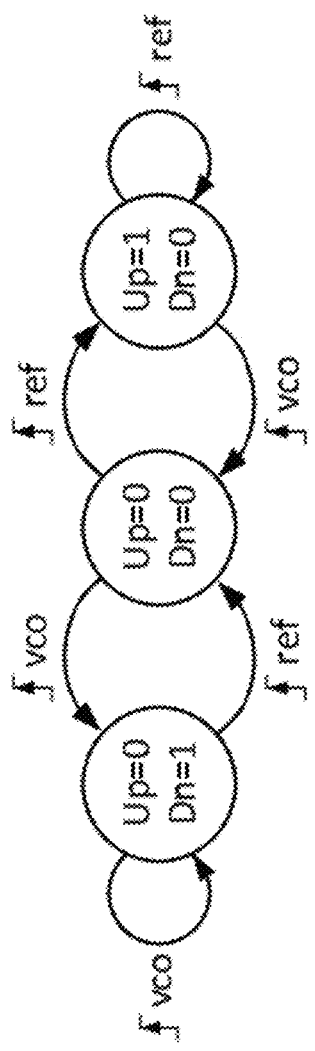
FIG. 37 illustrates an exemplary state diagram of the PFD.

FIG. 37 illustrates an exemplary state diagram of the PFD of FIG. 32. This state diagram shows that $V_{ctrl}$ can saturate to either VDD or GND when the frequency of the output of the VCO is higher or lower, respectively.

Figure 38:
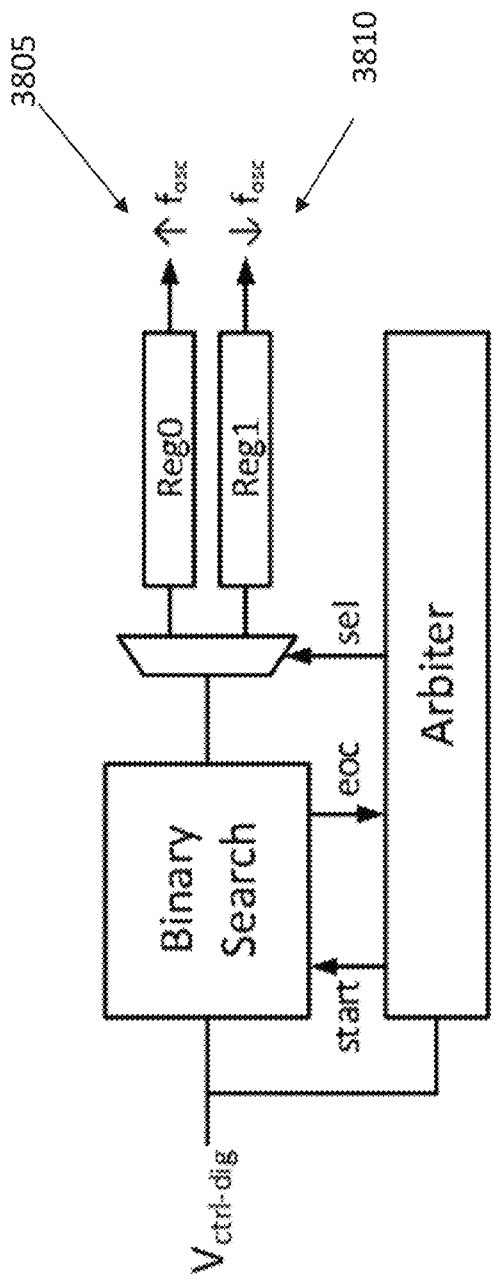
FIG. 38 illustrates an exemplary block diagram of the digital logic circuit of the PLL.

FIG. 38 illustrates an exemplary block diagram of the digital logic circuit of the PLL of FIG. 18. In some embodiments, a binary search algorithm can be implemented to adjust two digital registers to either increase (3805) or decrease (3810) the oscillation frequency of the VCO. As understood by the person skilled in the art, this process is similar to the logic that a successive-approximation register (SAR) analog to digital converter (ADC) uses. Thus, this algorithm can be termed as a SAR-like process.

Figure 39:
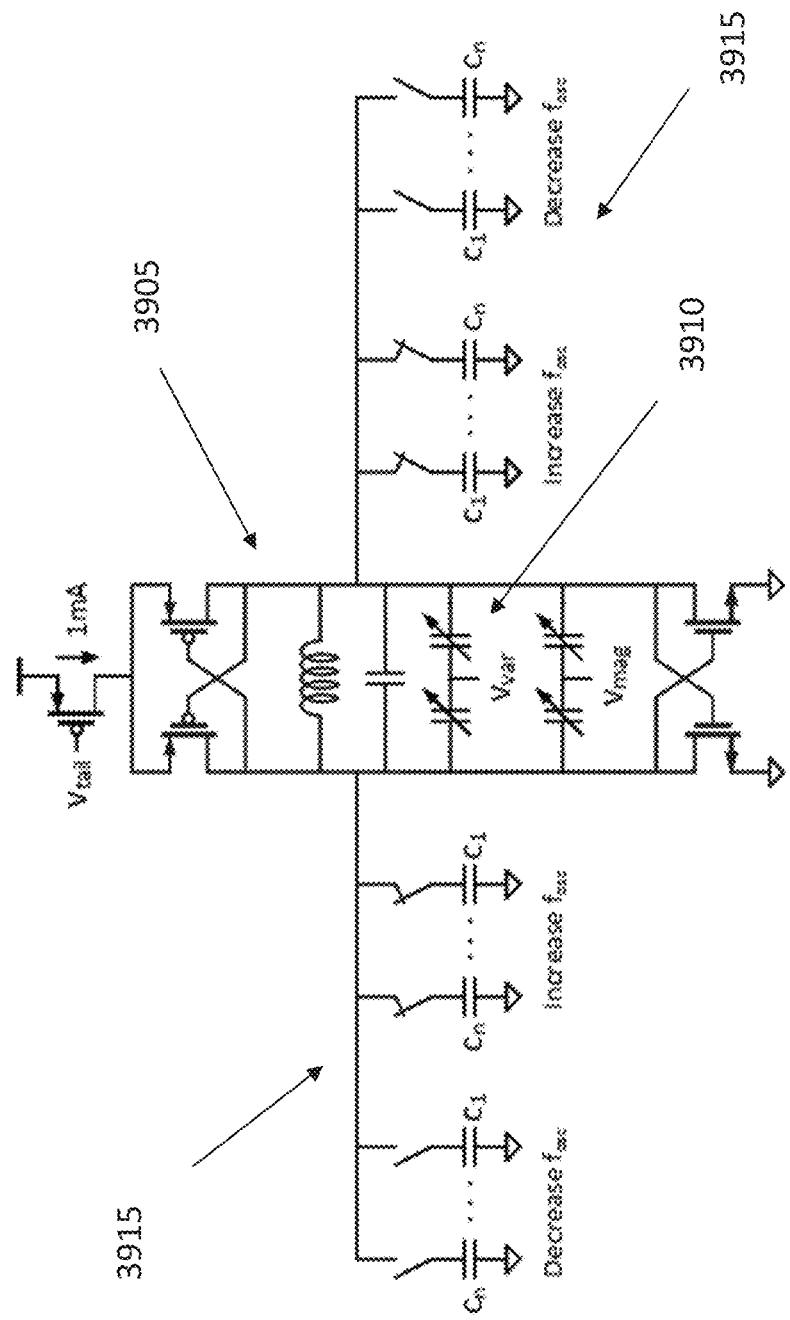
FIG. 39 illustrates an exemplary circuit schematic of the VCO.

FIG. 39 illustrates an exemplary circuit schematic of the VCO of FIG. 32. An LC oscillator (3905) can be used with n-type (NMOS) and p-type MOS (PMOS) negative resistor stages, and with a PMOS tail current. Switched differential binary-weighted capacitors (3915) can be added for digital course frequency tuning. Two CMOS varactors (3910) can provide the analog fine frequency tuning. For example, the current consumption of this stage can be 1 mA and the $K_{VCO}$ can be 500 kHz/V.

Figure 40:
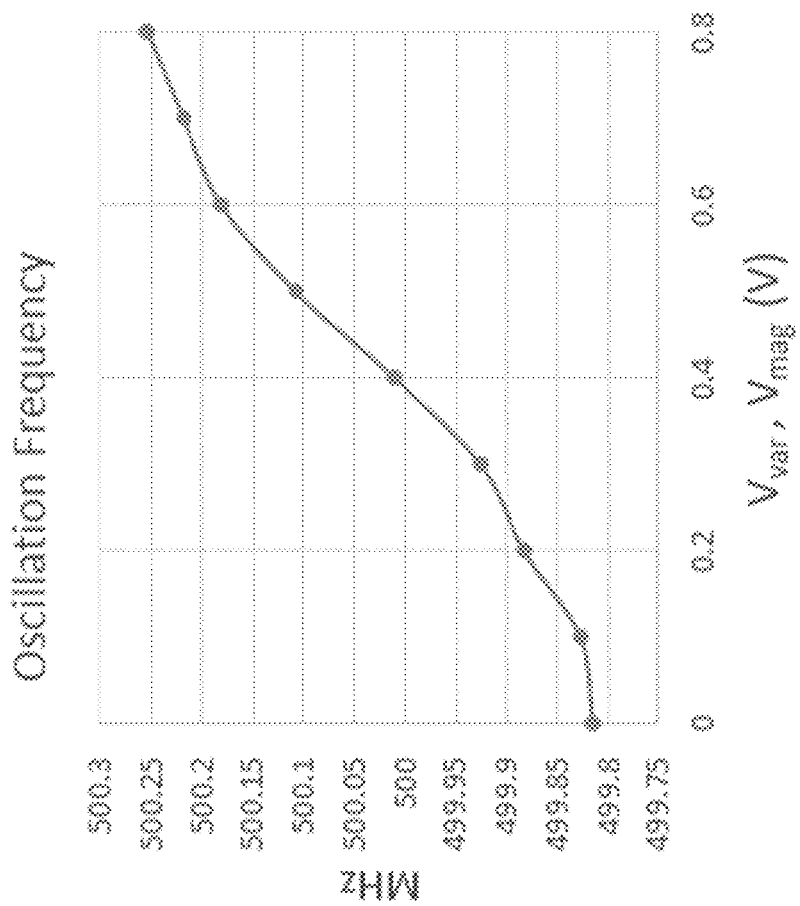
FIG. 40 illustrates exemplary simulation results of the VCO shown in FIG. 39.

FIG. 40 illustrates exemplary simulation results of the VCO show in FIG. 39.

When an LC oscillator is used in the PLL of the ATOMS device, the RF transmission signal can come directly from the oscillator itself. This can be possible if the sensitivity of the receiver in the external system is high enough to measure the signals coming from the oscillator.

Similarly, the output of the MAGFET can be integrated closely to the VCO to directly generate a frequency shift. Another alternative, in other embodiments, is to use a ring oscillator. This alternative can reduce the size and power consumption of the ATOMS device. In this case, a PA may be required.

Figure 41:
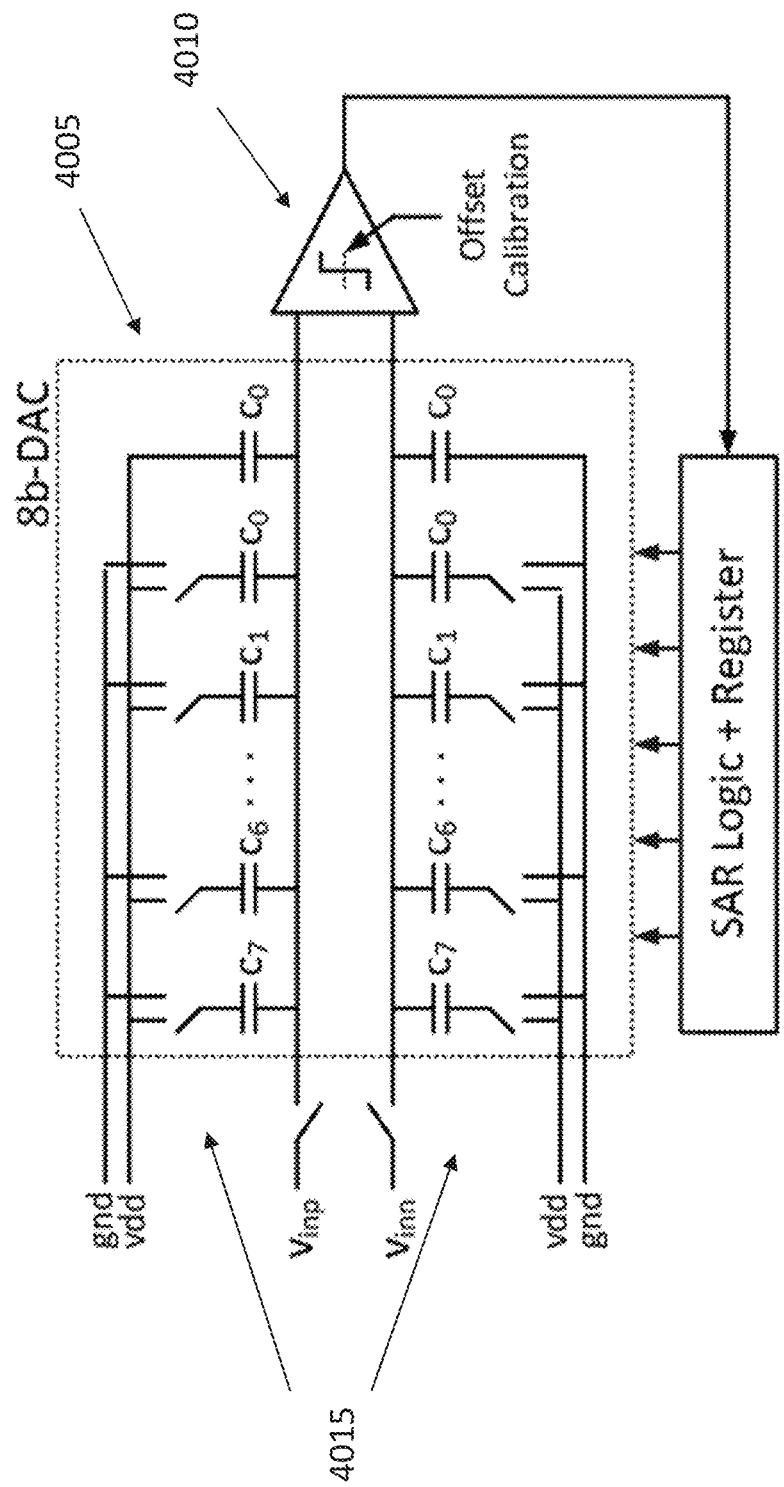
FIG. 41 illustrates an exemplary circuit schematic of the ADC.

FIG. 41 illustrates an exemplary circuit schematic of the ADC referred to above in the present disclosure. A charge-redistribution SAR ADC can be used to minimize power consumption. A differential 8-bit DAC (4005) with a comparator with offset calibration (4010) can be used. The differential DAC (4005) can use binary-weighted capacitors (4015).

Figure 42:
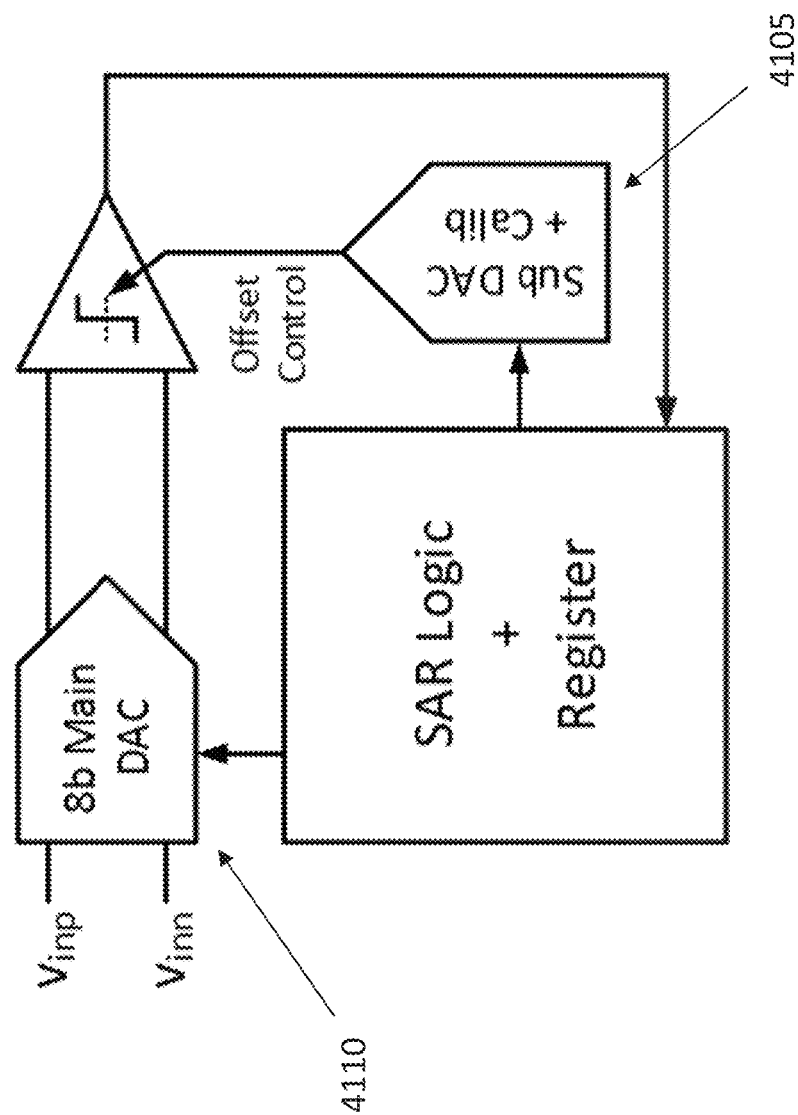
FIG. 42 illustrates an exemplary block diagram of the ADC.

FIG. 42 illustrates an exemplary block diagram of the ADC of FIG. 41. The resolution of the ADC (4110) can be improved if a Sub-DAC (4105) is added to the offset calibration. In this case, the Sub-DAC (4105) performs calibration and offset control that can increase the resolution of the ADC (4110).

Figure 43:
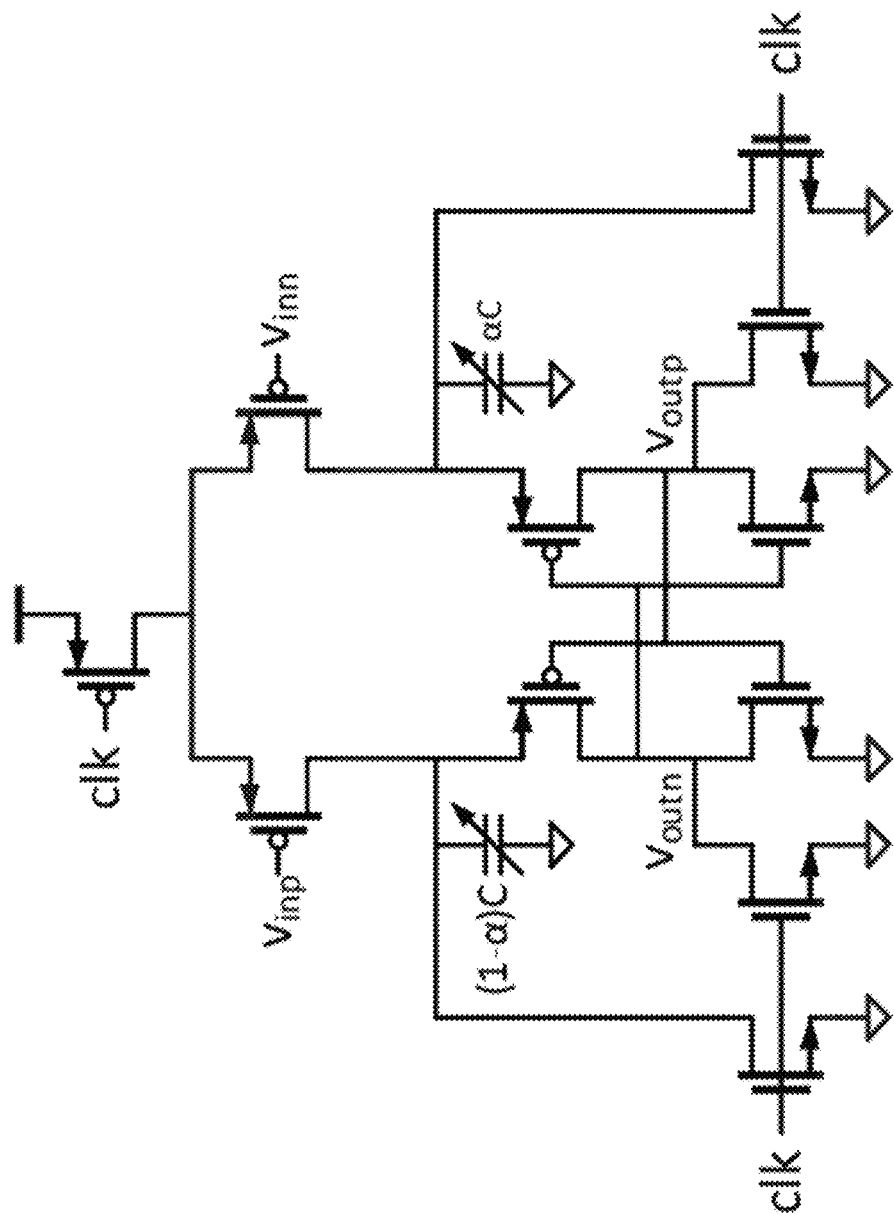
FIG. 43 illustrates an exemplary circuit schematic of the dynamic comparator.

FIG. 43 illustrates an exemplary circuit schematic of a dynamic comparator. This stage can use a strong-arm sense amplifier that uses a PMOS differential pair to minimize noise and has offset control via a differential capacitor digital to analog converter (DAC).

Figure 44:
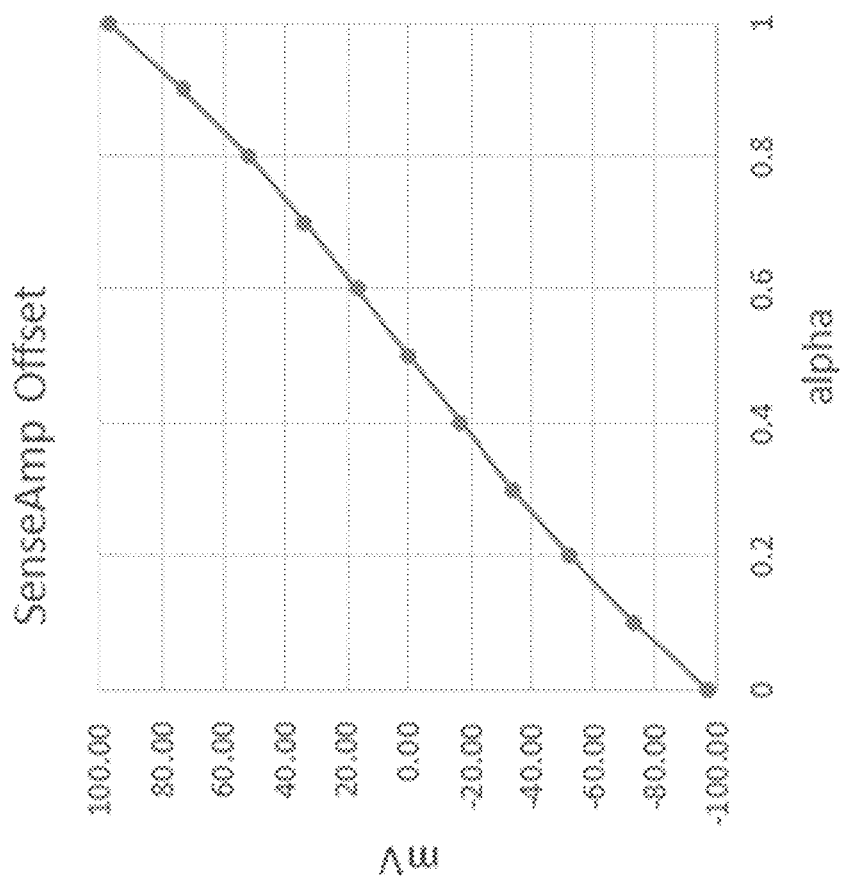
FIG. 44 illustrates exemplary simulation results of the offset control of the dynamic comparator shown in FIG. 43.

FIG. 44 illustrates an exemplary simulation result of the offset control of the dynamic comparator shown in FIG. 43. An offset control of ±100 mV can be achieved.

Figure 45:
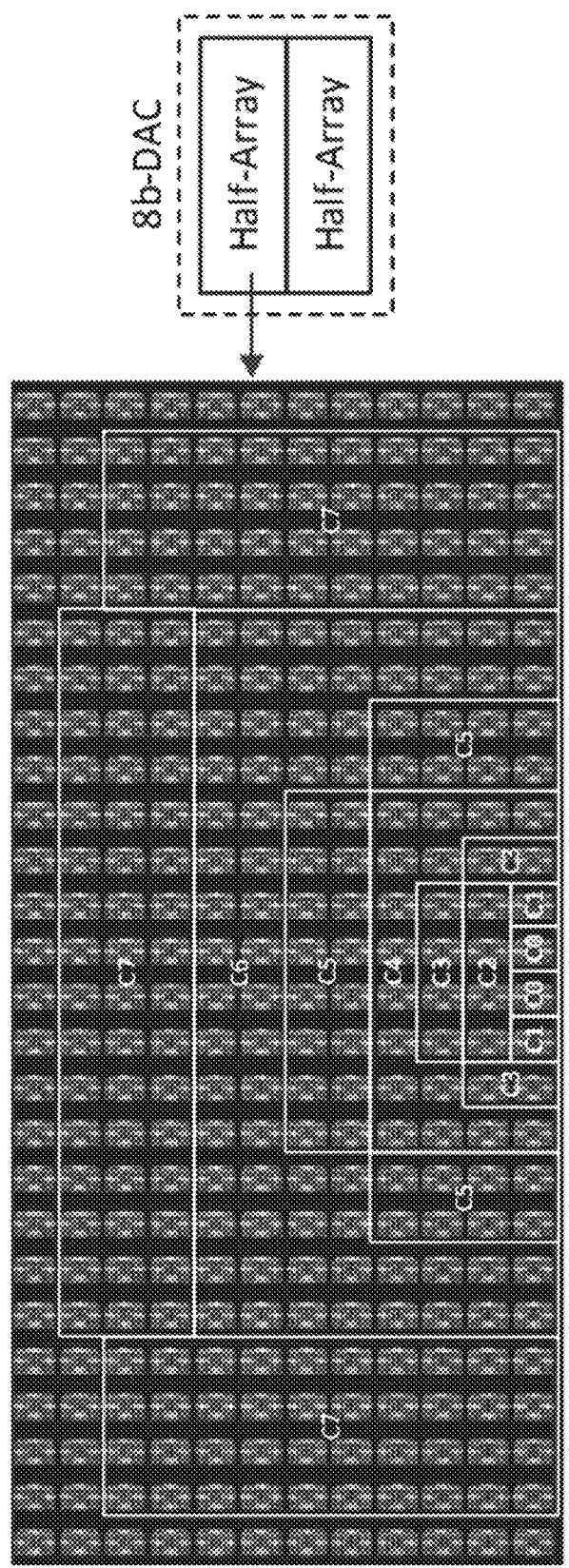
FIG. 45 illustrates an exemplary layout diagram of the 8-bit capacitor DAC of the ADC.

FIG. 45 illustrates an exemplary layout diagram of the 8-bit capacitor DAC of the ADC. For this DAC, two half-array structures are used. One half-array is shown with its common-centroid structure. The other half is mirrored based on the horizontal axis.

Figure 46:
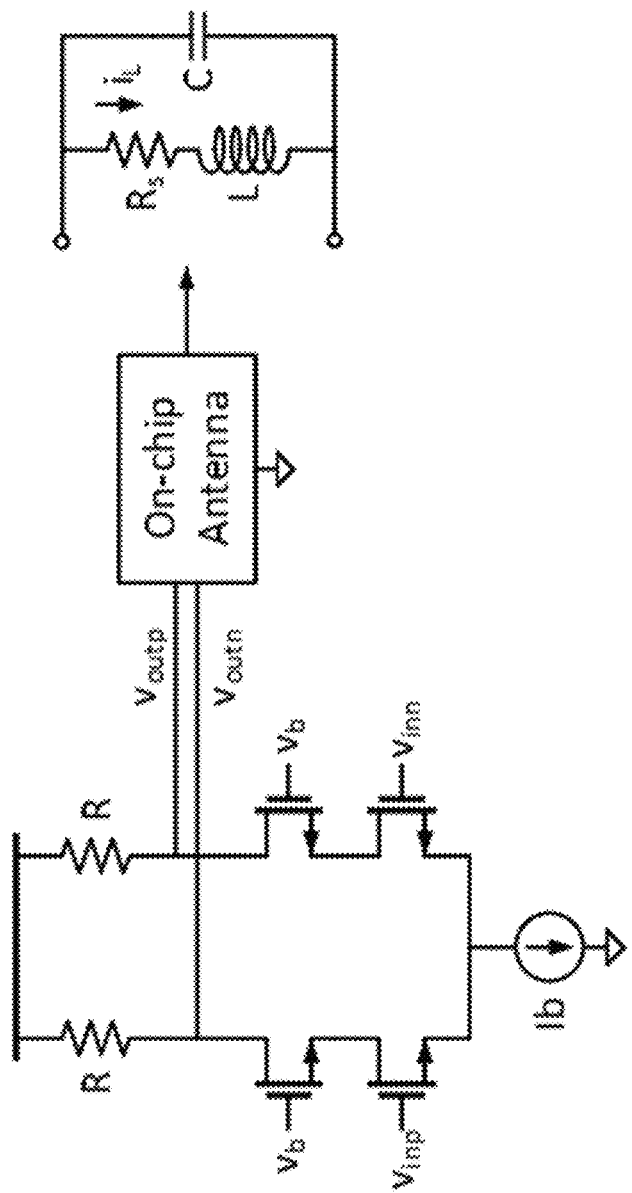
FIG. 46 illustrates an exemplary circuit schematic of the PA.

FIG. 46 illustrates an exemplary circuit schematic of the PA of FIG. 20. A differential cascade stage with resistive load can be used.

ATOMS can be tested in vitro in agarose phantoms simulating the electromagnetic properties of tissue. The ATOMS can be implanted into known locations within phantoms of approximately 5×5×5 cm size, and tested using MRI gradients, transmit-receive coils, and electronics operating at, for example, either 0-253 MHz or 500 MHz frequencies. Some tests may focus on quantifying magnetic field-dependent frequency signals and localization of a single implanted device. Subsequent tests can determine the ability to spatially resolve a plurality of ATOMS, such as, for example, two, ten or one-hundred ATOMS.

Another test may involve the detection of ATOMS in vivo by imaging implanted microsensors in living rats. For example, stereotactic surgery can be used to implant approximately ten ATOMS (encapsulated in parylene for biocompatibility) into different specific regions of the brain. The ATOMS can then be interfaced by using magnetic field gradients and RF signals as described herein and as understood by the person skilled in the art so as to demonstrate the ability to resolve each device's location. The precision of this localization can be checked by comparison to stereotactic implantation coordinates and conventional MRI scans (on which they will appear as dark spots).

Another test may involve the detection of ATOMS in vivo by monitoring the migration of these devices through the gastro-intestinal (GI) system of a mouse. This experiment can both provide an important practical proof of concept for this long-term technology, and launch an important short-term project in capsule endoscopy.

The methods, systems and devices of the present disclosure are an application of the physical principles of magnetic resonance imaging to localized wireless communication. As such, it provides an elegant solution to the problem of interfacing with distributed in vivo biosensors, and is expected to have substantial scientific and clinical impact. On the scientific front, many problems in biology require the study of physiological processes in their in vivo context. By developing ATOMS-powered biosensors and actuators and distributing them to appropriate organs such as the brain, vasculature, the GI tract, and the lymphatic system, biologists will be able to carry out new studies of disease-relevant processes in living animals. On the clinical front, there is major interest in advancing "small pill" technologies from single, centimeter-sized, wireless cameras to distributed micron-sized devices capable of migrating through the vasculature (or other orifices) and performing local imaging, sensing and interventions, thus reducing the need for invasive diagnostic and surgical procedures. The ability to adapt existing MRI systems to working with ATOMS can accelerate the initial adoption of this technology in academic laboratories. In some embodiments, custom ATOMS interfaces such, as a hand-held device, can be employed for outpatient and ambulatory deployment.

In the present disclosure, the ATOMS devices may comprise a magnetic sensor, which can be used to localize the single devices within a body, for example a biological body, through the use of a magnetic gradient field. The devices may also comprise additional sensors that can measure other quantities. For example, these additional sensors may measure biological quantities such as glucose levels in the bloodstream, or other biological or chemical quantities. The sensors may also be applied to non biological applications, for example sensing physical or chemical quantities within a structure or other non biological bodies.

In some embodiments, the shift in frequency of the electromagnetic waves emitted by the oscillator circuit of a device may be at least 1 ppm per Gauss, and the peak width of the emitted wave may be less than 160 ppm, therefore allowing a spatial resolution for the localization of 1 mm in a field gradient of 4000 Gauss per meter. The shift in phase may be at least 0.2 rad.

M some embodiments, the device may be configured to act in a desired way upon reception of a signal at its resonance frequency. Possible operating frequencies, for example, may be between 100 and 2000 MHz. In some embodiments, the device is configured to lock to a transmitted base frequency and to maintain its resonance frequency at the transmitted base frequency during subsequent reception and transmission of electromagnetic waves.

The devices may be able to determine their orientation in space due to the detection of the magnetic field. In some embodiments, the devices comprise a phase locked loop configured to keep its oscillation frequency for 4 ms after a reference signal is removed.

In some embodiments, the devices of the present disclosure could be used to sense the local chemical environment surrounding the devices. For example, the devices could include sensors whose current or voltage depends on local pH, salinity, or specific analyte concentrations (for example, neurotransmitters, hormones, growth factors, tumor factors, microbe-secreted factors, viral particles, gases), such that this current or voltage would be used by a logic circuit on the device to modulate its transmission of radiofrequency signals. These sensors could be based on electrochemical interfaces, nanotubes, nanofibers, or other similar technologies known to the person skilled in the art. Concentration gradients could be sensed by having more than one sensor on the device and comparing their relative measurements.

In other embodiments, the devices could sense local electric fields, for example, to enable the recording of neural activity. In this case, the logic circuit would be configured to convert aspects of neural signals (recorded via an electrode on the sensor) such as frequency, spike shape and amplitude, to modulated radiofrequency transmissions. In another alternative, the device could sense a physical property of its environment such as pressure. This can be accomplished, for example, using a microelectromechanical pressure sensor. In some embodiments, the devices can sense the impedance of the surrounding biological tissue by using electrodes connected to the target tissue.

In some embodiments, the devices can be inserted in a biological tissue by, for example, implanting, swallowing or injecting. In some embodiments, the location of the devices can be tracked over time, thereby allowing their temporal direction to be determined.

In some embodiments, the devices have an LC oscillator circuit which comprises a resistance, a capacitor and an inductor, as well as a transistor. In other embodiments, a ring oscillator can be used that comprises a resistance, a capacitor, an inductor and at least one transistor.

The methods and systems described in the present disclosure may be implemented in hardware, software, firmware or any combination thereof. Features described as blocks, modules or components may be implemented together (for example, in a logic device such as an integrated logic device) or separately (for example, as separate connected logic devices). The software portion of the methods of the present disclosure may comprise a computer-readable medium which comprises instructions that, when executed, perform, at least in part, the described methods. The computer-readable medium may comprise, for example, a random access memory (RAM) and/or a read-only memory (ROM). The instructions may be executed by a processor (for example, a digital signal processor (DSP), an application specific integrated circuit (ASIC), a field programmable logic array (FPGA), a graphic processing unit (GPU) or a general purpose GPU).

A number of embodiments of the disclosure have been described. Nevertheless, it will be understood that various modifications may be made without departing from the spirit and scope of the present disclosure. Accordingly, other embodiments are within the scope of the following claims.

The examples set forth above are provided to those of ordinary skill in the art as a complete disclosure and description of how to make and use the embodiments of the disclosure, and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

What is claimed is:

1. A method to sense a biological function, the method comprising:
   providing a device including
      a sensor to sense the biological function, and
      an oscillator circuit configured to change its resonance frequency upon application of a magnetic field;
   providing a communication device external to the biological tissue and configured to communicate through electromagnetic waves with the device implanted in the biological tissue;
   inserting the device in the biological tissue;
   applying a magnetic field gradient to the device; and
   spatially locating the device by its resonance frequency,
      wherein the device further includes
         a substrate,
         an antenna attached to a surface of the substrate, the antenna being substantially planar,
         the oscillator circuit on the surface of the substrate,
         a transmitter and receiver circuit on the surface of the substrate,
         a control logic circuit on the surface of the substrate, and
         the sensor on the surface of the substrate, the sensor comprising at least one magnetic sensor,
            wherein the antenna is configured to transmit and receive electromagnetic waves at a first frequency and a first phase between the device and the communication device,
            wherein the transmitter and receiver circuit are configured to operate the antenna,
            wherein the sensor is configured to sense an applied magnetic field, and to shift a transmitting or receiving frequency from the first frequency to a second frequency, or a transmitting or receiving phase from the first phase to a second phase, said shift being based on the applied magnetic field, and
            wherein the dimensions of the antenna and the oscillator circuit are configured to allow spatial localization of the device when the device is within a magnetic field gradient.

2. The method of claim 1, wherein the inserting the device in the biological tissue is carried out by implanting, swallowing or injecting.

3. A method to sense a biological function, the method comprising:
   providing a system, the system including a plurality of devices, each device including
      a sensor configured to sense a biological function, and
      an oscillator circuit configured to change a resonance frequency upon application of a magnetic field;
   providing a communication device external to a biological tissue and configured to communicate through electromagnetic waves with the plurality of devices implanted in the biological tissue;
   inserting the plurality of devices in the biological tissue;
   applying a magnetic field gradient to the plurality of devices; and
   spatially locating each device of the plurality of devices by its resonance frequency,
      wherein each of the plurality of devices further includes
         a substrate,
         an antenna attached to a surface of the substrate, the antenna being substantially planar,
         the oscillator circuit on the surface of the substrate,
         a transmitter and receiver circuit on the surface of the substrate,
         a control logic circuit on the surface of the substrate, and
         the sensor on the surface of the substrate, the sensor comprising at least one magnetic sensor,
            wherein the antenna is configured to transmit and receive electromagnetic waves at a first frequency and a first phase between the device and the communication device, wherein the transmitter and receiver circuit are configured to operate the antenna, wherein the at least one sensor is configured to sense an applied magnetic field, and to shift a transmitting or receiving frequency from the first frequency to a second frequency, or a transmitting or receiving phase from the first phase to a second phase, said shift being based on the applied magnetic field, and wherein the dimensions of the antenna and the oscillator circuit are configured to allow spatial localization of the device when the device is within a magnetic field gradient.

4. The method of claim 3, wherein the inserting the plurality of devices in the biological tissue is carried out by implanting, swallowing or injecting.

* * * * *